United States Patent [19]
Karellas

[11] Patent Number: 5,465,284
[45] Date of Patent: * Nov. 7, 1995

[54] SYSTEM FOR QUANTITATIVE RADIOGRAPHIC IMAGING

[75] Inventor: Andrew Karellas, Auburn, Mass.

[73] Assignee: University of Massachusetts Medical Center, Worcester, Mass.

[*] Notice: The portion of the term of this patent subsequent to Sep. 22, 2009, has been disclaimed.

[21] Appl. No.: 853,775
[22] PCT Filed: Dec. 5, 1990
[86] PCT No.: PCT/US90/07178
§ 371 Date: Jun. 2, 1992
§ 102(e) Date: Jun. 2, 1992
[87] PCT Pub. No.: WO91/09495
PCT Pub. Date: Jun. 27, 1991

Related U.S. Application Data

[63] Continuation-in-part of Ser. No. 446,472, Dec. 5, 1989, Pat. No. 5,150,394.
[51] Int. Cl.$^6$ .................................................. G01N 23/04
[52] U.S. Cl. ........................... 378/62; 378/54; 378/19; 378/98.9; 378/207; 250/252.1; 250/368; 250/370.09; 250/385.1; 250/580
[58] Field of Search ................. 378/62, 145, 146, 378/54, 156, 208, 19, 207, 98.9; 250/252.1, 370.09, 385.1, 368, 580

[56] References Cited

U.S. PATENT DOCUMENTS

| | | | |
|---|---|---|---|
| 3,803,417 | 4/1974 | Kok | 378/189 |
| 3,944,830 | 3/1976 | Dissing | 250/308 |
| 4,298,800 | 11/1981 | Goldman | 250/455 |
| 4,365,343 | 12/1982 | Grady et al. | 378/181 |
| 4,686,695 | 8/1987 | Macouski | 378/146 |
| 4,716,581 | 12/1987 | Barud | 378/198 |
| 4,829,549 | 5/1989 | Vogel et al. | 378/55 |
| 4,852,137 | 7/1989 | Mackay | 378/62 |
| 5,040,199 | 8/1991 | Stein | 378/146 |
| 5,090,040 | 2/1992 | Lanza et al. | 378/62 |
| 5,142,557 | 8/1992 | Toker et al. | 378/145 |
| 5,150,394 | 9/1992 | Karellas | 378/62 |
| 5,285,489 | 2/1994 | Ohtsuchi et al. | 378/156 |
| 5,289,520 | 2/1994 | Pellegrino et al. | 378/37 |

FOREIGN PATENT DOCUMENTS

| | | |
|---|---|---|
| 0253742 | 1/1988 | European Pat. Off. . |
| 0265302 | 4/1988 | European Pat. Off. . |
| 2412161 | 9/1974 | France . |
| WO89/11826 | 12/1989 | WIPO . |

OTHER PUBLICATIONS

"Binning Spectral Images in a Charge–Coupled Device", Epperson et al., *Amer. Chemical Society*, Jul. 1989, pp. 1513–1519.
"Molecular Fluorescence Measurements with a (List continued on next page.)

*Primary Examiner*—Georgia Y. Epps
*Assistant Examiner*—Kim-Kwok Chu
*Attorney, Agent, or Firm*—Hamilton, Brook, Smith & Reynolds

[57] ABSTRACT

A system for spectroscopic imaging of bodily tissue in which a scintillation screen and a charged coupled device (CCD) are used to accurately image selected tissue. Applications include the imaging of radionuclide distributions within the human body or the use of a dual energy source to provide a dual photon bone densitometry apparatus that uses stationary or scanning acquisition techniques. X-rays are generated by an x-ray source which pass through a region of a subject's body, forming an x-ray image which reaches the scintillation screen. The scintillation screen reradiates a spatial intensity pattern corresponding to the image, the pattern being detected by a CCD sensor. The image is digitized by the sensor and processed by a controller before being stored as an electronic image. A dual energy x-ray source that delivers two different energy levels provides quantitative information regarding the object being imaged using dual photon absorptiometry techniques.

60 Claims, 14 Drawing Sheets

OTHER PUBLICATIONS

Charge–Coupled Device Detector", Epperson, et al., *Anal. Chem.* vol. 61, pp. 282–285 (Feb. 1989).

"Imaging system with an amorphous silicon linear sensor", Hasegawa, *Rev. Sci. Instrum.* vol. 60 (7), Jul. 1989, pp. 2284–2286.

"X–ray imaging with two–dimensional charge–coupled device (CCD) arrays", Herron, et al., Abstract *SPIE* vol. 486, (1984) pp. 141–145.

"X–ray Imaging with Two–Dimensional CCD Arrays", Kennedy, et al., *AAPM Annual Meeting Program*, p. 504.

"Energy–modulated x–ray microtomography", Kinnedy et al., *Rev. Sci. Instrum* vol. 59 (1) Jan. 1988, pp. 196–197.

"Digital Slot scan mammography using CCDs", Nelsen et al., Abstract.

"Prototype performance of a high resolution x–ray Imaging system for use in coronary angiography", Roehrig et al., Abstract.

"Development of a High Resolution X–ray Imaging Device For Use in Coronary Angiography", Roehrig et al., Abstract, *SPEI* vol. 767 Medical Imaging (1987), pp. 144–153.

SYSTEM FOR QUANTITATIVE RADIOGRAPHIC IMAGING

This application is the U.S. National phase application and claims priority to International Application No. PCT/US90/07178 filed on Dec. 5,1990, and is a continuation-in-part application of U.S. Ser. No. 07/446,472 filed on Dec. 5,1989, now U.S. Pat. No. 5,150,394.

BACKGROUND OF THE INVENTION

In recent years the use of radiological examining equipment to make measurements of bone density in patients has continually increased. In particular, the use of such equipment in diagnosing and analyzing osteoporosis has become prevalent in the medical community. Osteoporosis is characterized by the gradual loss of bone mineral content or atrophy of skeletal tissue, resulting in a corresponding overall decrease in average bone density. Such a condition is common in elderly women and greatly increases the risk of fracture or similar bone related injury.

The presently available techniques for the radiological measurement of bone density utilize a rectilinear scanning approach. In such an approach, a radiation source, such as a radionuclide source or an x-ray tube, and a point detector are scanned over a patient in a raster fashion. This scan results in an image which has been derived from the point-by-point transmission of the radiation beam through the bone and soft tissue of a patient. The calculation of the bone-mineral concentration (the "bone density") is usually performed by a dual energy approach.

The current rectilinear scanning approach is generally limited by its long scanning time and its lack of good spatial resolution. The poor spatial resolution results in an inability to provide an image displaying high anatomical detail and which will permit accurate determination of the area in the scan occupied by bone. Moreover, the output of the x-ray source and the response of the detector must be closely monitored in order to assure high accuracy and precision.

SUMMARY OF THE INVENTION

In accordance with the present invention, a stationary bone densitometry apparatus is provided for examining a subject's body. A dual energy x-ray source directs a beam of x-ray radiation toward the subject's body. The radiation is applied to the entire region of the body being examined. A scintillation screen receives the x-ray radiation passing through the body of the subject, and emits radiation in the visible spectrum with a spatial intensity pattern proportional to the spatial intensity pattern of the received x-ray radiation.

A charge coupled device (CCD) then receives radiation from the scintillation screen. This CCD sensor generates a discrete electronic representation of the spatial intensity pattern of the radiation emitted from the scintillation screen. A focusing element between the screen and the CCD sensor focuses the scintillation screen radiation onto the CCD sensor. To prevent ambient radiation from reaching the CCD sensor, the present embodiment employs a shade or hood surrounding a region between the scintillation screen and the CCD sensor. A CCD controller then processes the electronic representation generated by the CCD sensor, and outputs corresponding image data.

A dual photon x-ray source is used to allow the examination to be performed with x-rays at two different energy levels. This source can be an x-ray tube, or a radionuclide source with a filter element to remove one of the energy levels when desired. Correlation of the image data retrieved using each of the two x-ray energy levels provides quantitative bone density information.

A focusing element between the scintillation screen and the CCD sensor can take the form of a lens or a fiber optic reducer. An image intensifier can be used in conjunction with the CCD sensor. The image intensifier can be a "proximity type" image diode or a microchannel based device. It can also be directly attached to the CCD. An image store used with the CCD controller allows manipulation of the CCD sensor output signals by a data processor. This includes the correlation of measurements utilizing x-ray beams of two different energy levels. The system can also be adapted to operate at higher shutter speeds enabling the counting of x-ray transmissions. This provides energy measurements of x-ray transmissions that are useful in certain applications.

An additional preferred embodiment is directed to systems and methods of imaging spectroscopy where a charge coupled device (CCD) is optically coupled to a scintillator and measures or counts the spatial intensity distribution of a radionuclide that has been introduced into bodily tissue, either in vivo or in vitro. CCD's of sufficient thickness can be used to measure gamma ray events without the use of a scintillator in certain applications. The CCD has sufficient resolution and sensitivity to measure such distributions accurately, usually in less than two minutes. Radiation sources that emit radiation having an energy in a range between 10 and 2,000 keV, and preferably in the range between 20 and 600 keV, are delivered to the cancerous tissue or any other suitable pathologic abnormality.

The CCD acquires "frames" of information by counting the number of gamma-ray events over a selected period of time. Each frame, or a sequence of frames that have been added or summed to provide an image, can be filtered using pulse height analysis techniques to substantially reduce or eliminate scattered radiation. Pulse height analysis can also be utilized to discriminate between signals having different energy levels that contain diagnostically significant information. The system's discrimination and energy measuring capabilities render it suitable for diverse applications.

DETAILED DESCRIPTION OF THE PREFERRED EMBODIMENTS

Figure 1:
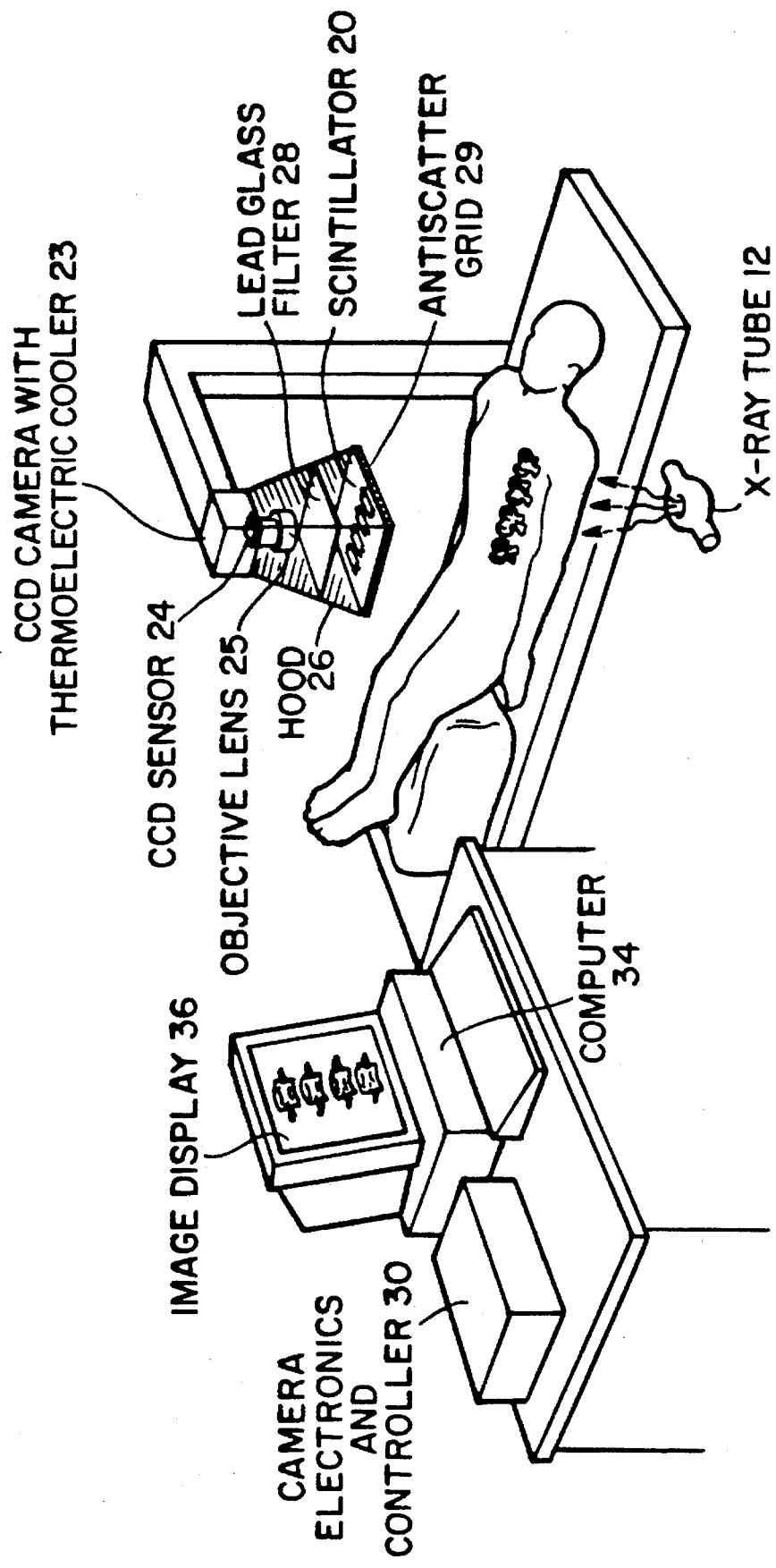
FIG. 1 is a perspective view of the imaging system of the present invention.

In FIG. 1 a preferred embodiment of the invention for performing bone densitometry studies uses a detector 10 and either an x-ray tube 12 or a radionuclide radiation source such as Gadolinium-153. The detector 10 comprises a scintillating plate 20 which is optically coupled to a two-dimensional charge-coupled device 24 (CCD). The CCD is a two dimensional array of detectors integrated into a single compact electronic chip. The optical coupling between the scintillating plage 20 and the CCD 24 is accomplished by an optical grade lens 25. Such a lens should have a low f-number (0.6–1.8) for adequate light collection from the screen. The collection efficiency (E) of light from the scintillating plate emitted in the direction of the CCD can be computed by the equation:

$$E = \frac{t\,m^2}{4f^2(m+1)^2}$$

Figure 2:
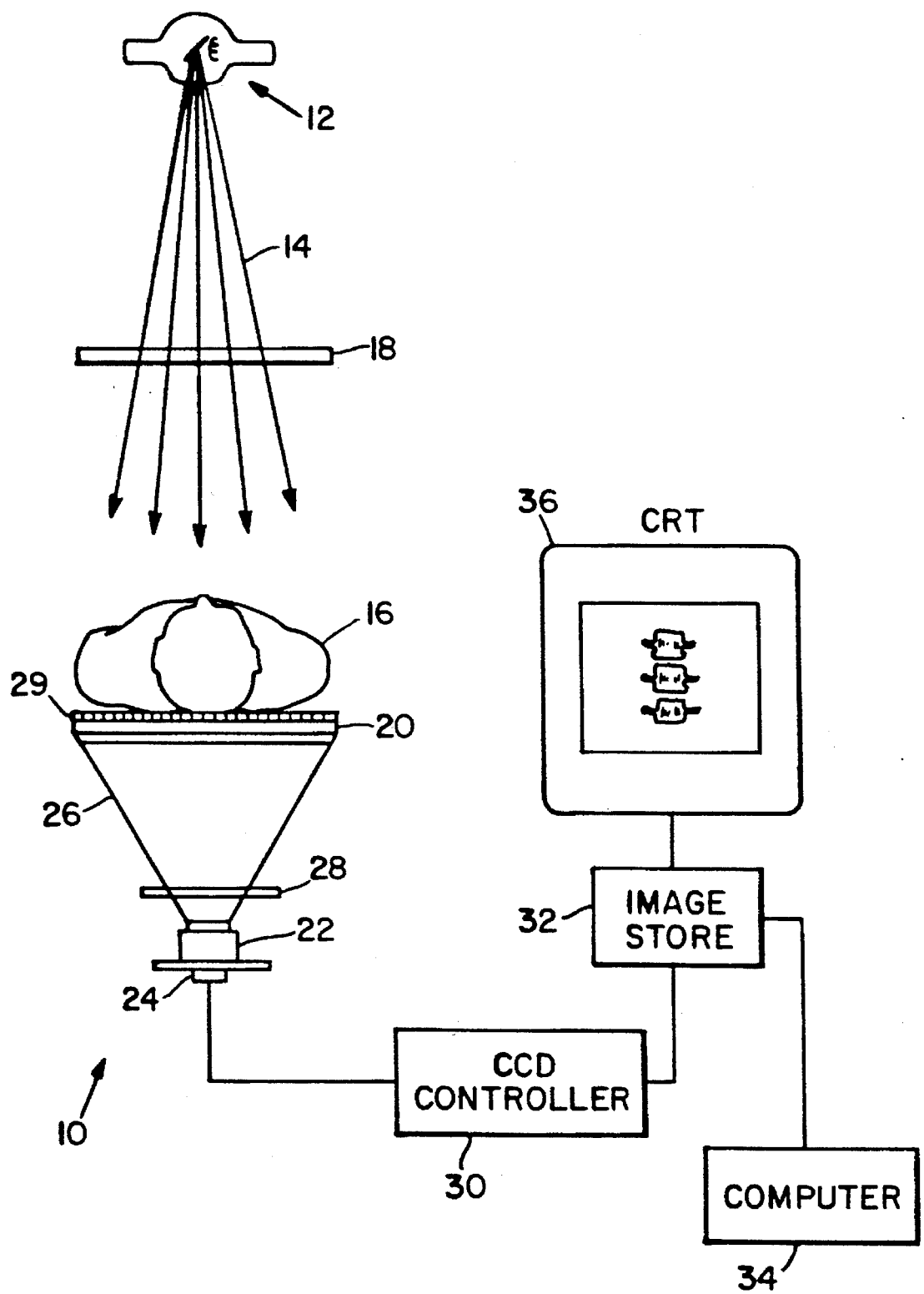
FIG. 2 illustrates in schematic view a bone density measuring apparatus using a lens to focus image data from a scintillation onto a CCD sensor.

In an alternate approach, the optical coupling between the scintillating plate and the CCD can be performed with a fiberoptic reducer. Referring to FIG. 2, a bone densitometry apparatus 10 has an x-ray tube 12 which delivers a beam of x-rays 14 towards the body of a subject 16 being examined. The x-ray tube is capable of emitting x-ray radiation at each of two distinct energy levels. The two energy levels are used to obtain two distinct x-ray images of the patient, as is discussed later. Note in comparison to FIG. 1, the source can be positioned above the patient and the detector below the table.

When the subject 16 is irradiated with the x-ray energy, a percentage of the x-rays reaching the subject 16 is absorbed by the subject's body, the amount of absorption depending on the density of bone or tissue upon which the x-rays are incident. Since x-rays generally travel in a straight line, the x-ray energy exiting the subject's body on the side of the body away from the source 12 is a spatial representation of absorption in the subject's body, and therefore of relative tissue and skeletal densities.

To receive the x-rays passing through the subject's body, a scintillation screen 20 is provided on the side of the patient away from the x-ray source 12. The scintillation screen 20 is a fluorescent material sensitive to x-rays, and when it receives x-ray energy it reradiates visible light. The spatial intensity patterns of the radiation emitted from the scintillation screen is proportional to the spatial intensity pattern of the x-ray radiation received by the screen 20. Thus the scintillation screen 20 provides an image in the visible spectrum, or alternating in the ultraviolet or near infrared, which is regionally proportional to the x-ray image reaching the scintillation screen 20.

A lens 22 is positioned between the scintillation screen 20 and a CCD sensor 24. The CCD sensor 24 is an array of photosensitive pixels using closely spaced MOS diodes which convert photons to electrons and thereby generate a discrete electronic representation of a received optical image. The lens 22 faces the scintillation screen and focuses the visible light emitted from the scintillation screen 20 through the lens 22 and onto the surface of the CCD sensor 24. In order to prevent ambient light from reaching the CCD sensor, a shade surrounding the region between the scintillation screen 20 and the lens 22 is provided in the form of a photographic bellows 26. The shading of bellows 26 serves to reduce the optical noise level of the image signal reaching the CCD sensor 24.

Although the scintillation screen 20 absorbs most of the x-rays incident upon it, some may still be transmitted through the screen 20 and interfere with the optical image signal of the scintillation screen 20. The direct interaction of x-rays with a CCD sensor produces very bright pixels resulting in a "snow" effect in an optical image detected by the sensor. In addition, prolonged direct x-ray irradiation of a CCD sensor can increase its dark current. For these reasons, an optical grade lead-glass or lead acrylic filter 28 is positioned between the scintillation screen 20 and the lens 22 or alternatively, between the lens and the CCD. The lead-glass filter 20 absorbs most of the stray x-rays and prevents them from reaching the CCD sensor 24. An anti-scatter grid is used between the patient and scintillation screen for preventing scattered x-rays from reaching the screen.

During a typical examination, the subject 16 is placed between the x-ray source 12 and the scintillation screen 20. The x-ray source is then activated for a short time interval, typically one to five seconds. As x-rays are differentially transmitted and absorbed through the body of the subject 16, they interact with the scintillation screen 20. Upon interaction, the screen 20 emits light in the visible part of the electromagnetic spectrum. In the present embodiment, the scintillation screen is a terbium-activated material and emits light in the region of 540 nm.

The light emitted from the scintillator is transported to the CCD sensor via the lens 22. Upon interaction with the CCD sensor 24, light energy is converted into electrons which are stored in each pixel of the CCD sensor 24. The CCD sensor 24 of the present embodiment consists of 512×512 pixels, but such sensors come in a number of different sizes. The CCD sensor "integrates" the image signal from the scintillation screen in that it senses the optical image and stores charge during the entire x-ray exposure interval. After termination of the x-ray exposure, the discrete representation in the CCD 24 is read out by CCD controller 30. The CCD controller 30 reads the image representation from the CCD sensor 24 pixel by pixel and organizes it into a digital array. The digital array, representing spatial position and x-ray intensity, is then output to a memory or image store 32. From the image store 32, the image can be accessed by a data processor 34 for performing image processing techniques. A cathode ray tube (CRT) 36 is also provided to allow the image to be displayed before or after processing by data processor 34.

Unlike other conventional detection schemes, such as film screen radiography, CCD-based imaging provides a linear quantitative relationship between the transmitted x-ray intensity and the charge generated in each pixel of the CCD. After the first high energy x-ray exposure is acquired, the resulting image is stored in image store 32 and a second exposure with a low energy x-ray beam is acquired with the subject 16 in the same position. During this exposure, a low energy x-ray beam is used which is typically at about 70 kVp with a tube current at about 1 mA. The tube is capable of accelerating electrons at 40 kVp and up to approximately 140 kVp. Note that the tube potential and current are controlled by the computer menu. The low energy x-ray image is then stored in image store 32 with the high energy exposure. Each image provides quantitative information about the relative transmission of x-rays through soft tissue and bone.

Once both images are obtained, comparative processing techniques of dual photon absorptiometry are applied to determine quantitative density measurements of those body regions scanned by the x-rays. The correlation of two images generated by x-rays of two different energy levels over a short time interval results in the substantial reduction in the likelihood of systematic pixel-by-pixel errors caused by instability of the x-ray tube output.

Because the present embodiment of the invention is concerned with an area detector as opposed to a scanning detector, the measurement time necessary for a densitometry examination is greatly reduced. Rather than scanning across the region to be examined in a rectilinear fashion, the entire region is irradiated simultaneously and the resulting image processed simultaneously. Typically, the entire procedure using the present dual photon technique lasts 30 to 60 seconds, depending on the power of the x-ray tube and processing speed of the supporting electronics.

Figure 3:
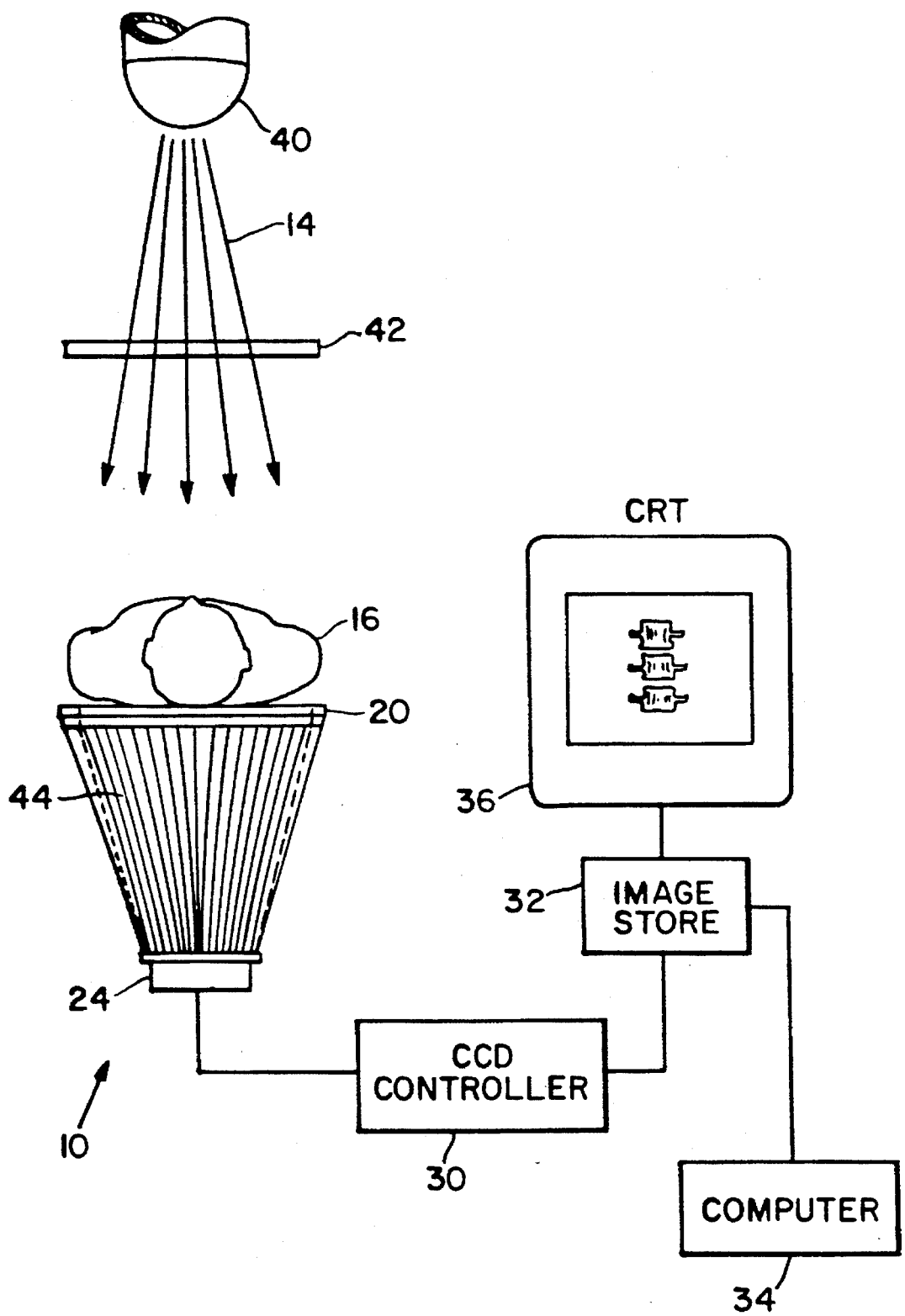
FIG. 3 illustrates in schematic view a bone density measuring apparatus using a fiber optic reducer to deliver an image from a scintillation screen to a CCD sensor.

FIG. 3 shows an alternative embodiment to that of FIG. 2. In this embodiment, the x-ray tube source 12 of FIG. 2 is replaced with radio-nuclide source 40. The radionuclide source is gadolinium-153. Gadolinium-153 emits photons simultaneously in two energy bands, a lower energy band of 44 keV and an upper energy band of 100 keV. Thus, the gadolinium source is a dual photon radiation source. In order to allow the images from the two different energy levels to be obtained separately, an x-ray filter 42 is placed between the source 40 and the subject 16. In the present embodiment, the filter 42 is copper or a K-edge filter, and eliminates nearly all of the low energy (44 keV) emission from the beam. Removal of the filter restores the beam to its dual energy nature. The filter 42 is implemented as an electromagnetic shutter which may be opened and closed in the line of the x-ray beam. A high energy image is acquired first with the filter shutter closed, after which an image is obtained using the dual energy beam with the shutter open.

Both electronic images are stored, and an image representative of the transmission of only the low energy photons is obtained by electronically subtracting the high energy image from the dual energy image with the data processor 34. Once both images are obtained, comparative dual photon processing techniques are used to make quantitative density calculations.

An additional feature of the embodiment of FIG. 3 is the replacement of the lens 22 of the FIG. 2 embodiment with a fiber optic reducer 44. The fiber optic reducer 44 is a focusing device consisting of a large array of optical fibers packed tightly together, and leading from the scintillating screen 20 to the CCD sensor 24. Near the CCD sensor 24, many of the fibers can be fused together, thus combining the signals present on individual fibers. The effect is a compression of the image from the input of the reducer 44 at the scintillation screen 20 to the reducer output at the CCD sensor 24. In this manner, the reducer 44 effectively focuses light from the scintillating screen 20 onto the CCD sensor 24 without the necessity of a lens for the focusing region.

Although they are shown together in FIG. 3, it is not necessary to use the fiber optic reducer 44 with the radionuclide source 40. Either element can be substituted into the configuration of FIG. 2 individually. The x-ray filter 42, however, should be used with the radionuclide source 40 to provide a dual photon discrimination capability. Note, however, that pulse height analysis can be performed in conjunction with the embodiment of FIGS. 10 & 11.

Figure 4:
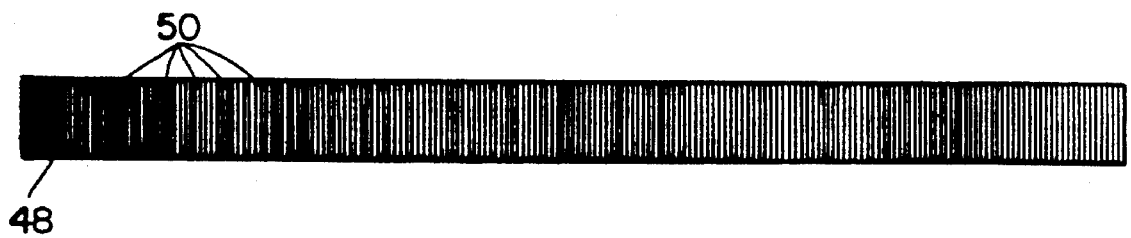
FIG. 4 illustrates another preferred embodiment for the scintillation screen employing a fiberoptic plate.

FIG. 4 shows an alternative to the scintillation screen 20 of FIGS. 2 and 3. The screen 48 depicted by FIG. 3 is a scintillating fiber optic plate. The plate 48 is a fiber optic faceplate consisting of scintillating fibers 50 running through the plate. The fiber optic plate is optically interfaced to the CCD in essentially the same way as the scintillation screen 20 of FIG. 2, but the fiber optic plate 48 allows for greater quantum efficiency due to increased x-ray stopping capability.

Figure 5:
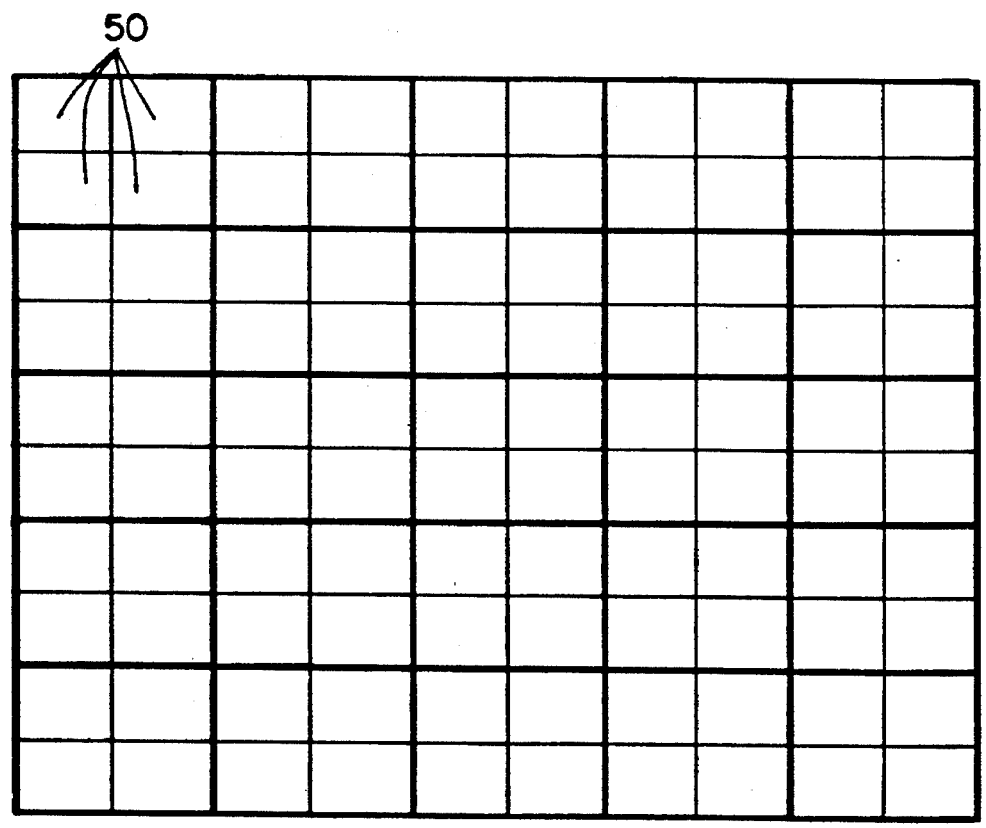
FIG. 5 is an illustration of the pixel array of a binnable CCD sensor.

Shown in FIG. 5 is a representation of the pixel array of the CCD sensor 24. The array shown in FIG. 5 is only 10×10 for illustrative purposes, and the actual array can be of different dimension. Each pixel in the array is an individual photosensitive element which contributes to the overall image detected by the array. A feature of the CCD sensor of the present embodiment is the capability of the pixels of the sensor 24 to be "binned" together. The binning of the pixel array refers to the ability of the sensor electronics to combine groups of pixels together to form "super pixels" which are then identified as single picture elements.

Charge is binned by combining charge packets contained in two or more adjacent potential wells into a single potential well during charge readout. Serial and parallel binning can be combined to perform two dimensional binning from any rectangular group of wells or detector elements.

The dark lines in the binnable array of FIG. 5 illustrate where individual pixels might be grouped together. For example, the four upper left hand corner pixels 50 can be binned together through control of the CCD sensor 24 to form a super pixel. The super pixel is then identified by the CCD electronics as a single pixel, the light intensity reaching each pixel 50 being averaged across the surface of the entire super pixel. In this manner, the dimension of the array can be electronically controlled. As can be seen in FIG. 5, if groups of four pixels are binned together across the 10×10 array, the overall array dimension becomes 5×5. Although the binning of the CCD sensor 24 reduces the resolution of the pixel array, the relative percentage of noise is also reduced, thus providing an improved signal to noise ratio.

The following x-ray data acquisition approach is an alternative to the one described above. In this approach, an image is acquired at high energy and the CCD is read in the normal non-binned mode. Due to the high penetration of the high energy beam through the body, the x-ray fluence exiting the body is high as compared to that of the low energy beam. Therefore, the resulting charge signal per CCD pixel is relatively strong. This image is stored as the high energy image. Also, this image is used in order to compute the area of the bone to be measured by manual selection of the region of interest or by automatic edge detection. Therefore, we take advantage of the high resolution image for greater accuracy in the measured bone area. Previously, the accuracy and precision of bone density measurements are limited to a great extent by suboptimal spatial resolution. The next image which is acquired with low energy is read out by the pixel binning approach, e.g. using a 2×2 pixel binning. The transmission of the low energy beam through the body is low as compared to the high energy beam. Therefore, in order to record a strong signal in each CCD pixel we must increase the radiation dose.

Alternatively, the binning technique can be used for the low energy in order to increase the signal to noise ratio and to a decrease the radiation dose. This dual mode acquisition procedure is a very powerful tool for improving the signal to noise ratio and lowering the radiation dose to the patient.

Figure 6:
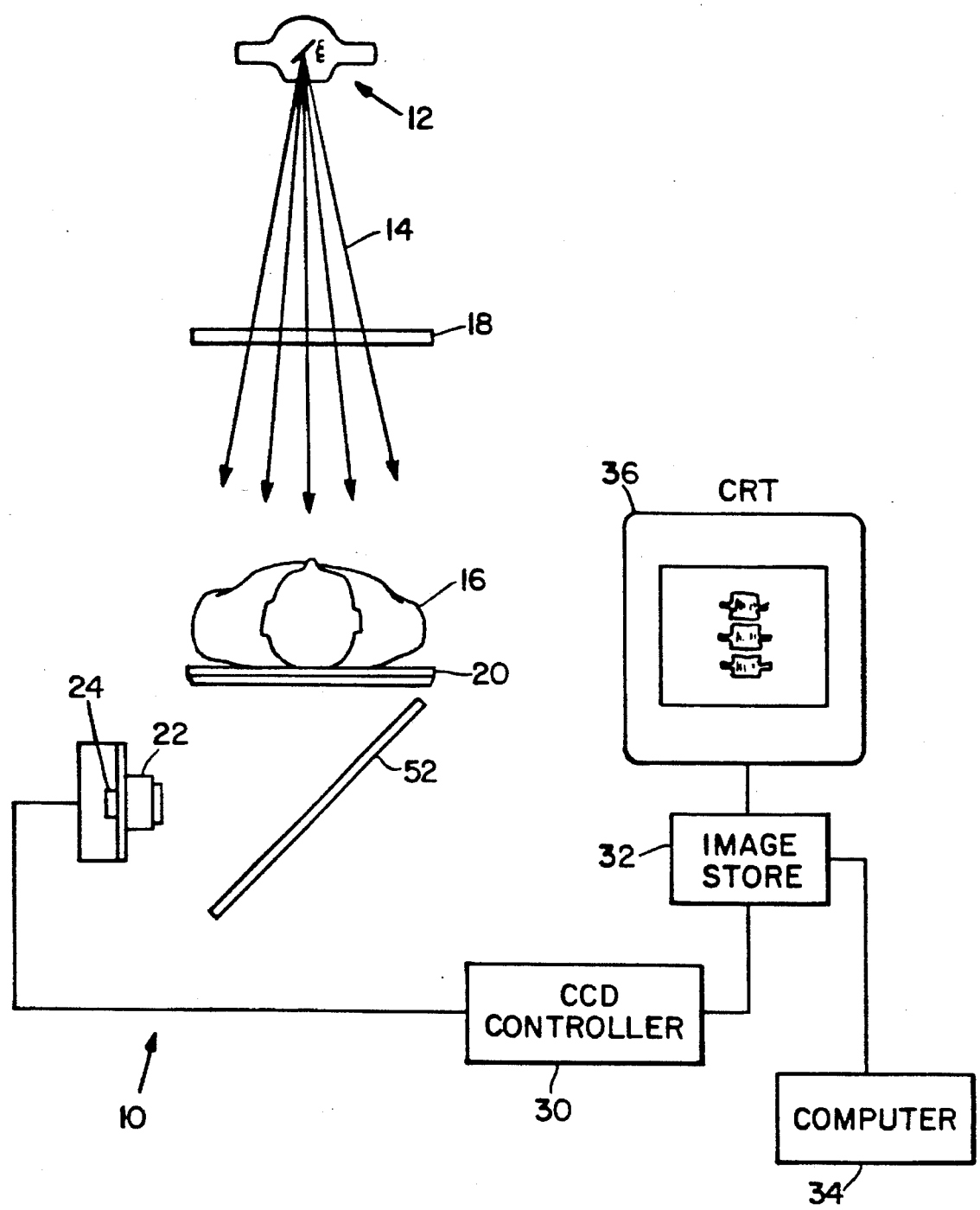
FIG. 6 is an alternative preferred embodiment to the bone density measuring apparatus of FIG. 2.

Although the arrangement of optical elements as shown in FIGS. 2 and 3 represent preferred embodiments, the functionality of the system is not dependent upon such an in-line type of optical transmission. FIG. 6 shows an alternative arrangement of optical elements where the CCD sensor 24 is set at an angle relative to scintillation screen 20, and mirror 52 is used to reflect the radiation given off by the scintillation screen toward the CCD sensor 24. Lens 22 is shown between CCD sensor 24 and mirror 52 and focuses the image onto the CCD sensor. However, the focusing of the scintillation screen image can take place before or after the image reaches mirror 52. In fact, the mirror itself may be shaped to provide focusing of the image from the scintillation screen 20.

Figure 7:
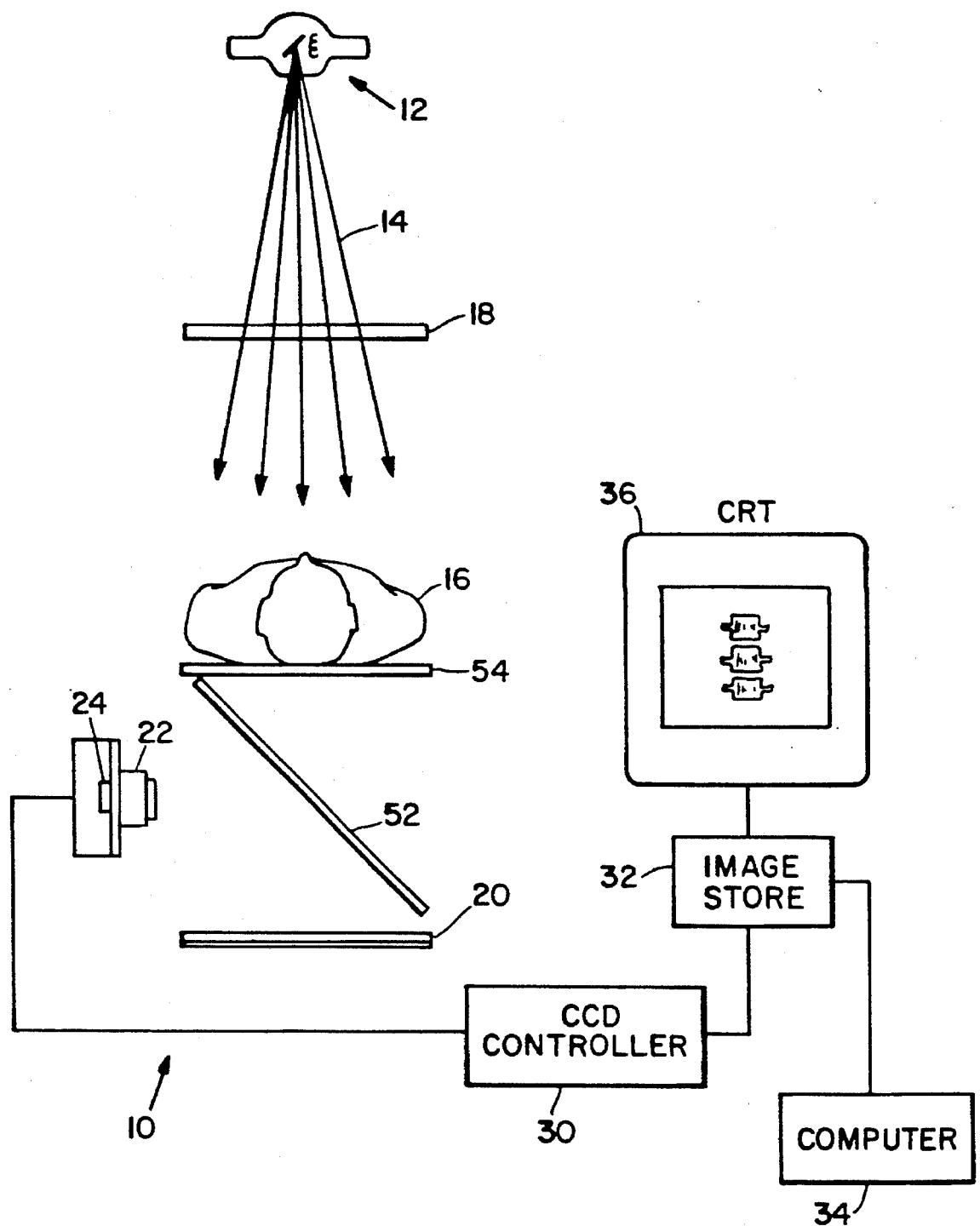
FIG. 7 is another alternative preferred embodiment to the bone density measuring apparatus of FIG. 2.

FIG. 7 shows another alternative arrangement of optical components. In FIG. 7 the subject 16 is suspended by a support 54 which is transparent to x-rays. The support 54 keeps the subject 16 elevated a distance above scintillation screen 20. As the x-rays reach scintillation screen 20, the screen 20 reradiates image data from the same surface upon which the x-ray radiation is incident. Mirror 52 is now aligned to reflect this image towards CCD sensor 24 which collects the image as focused through lens 22 to be processed by the CCD controller 30.

As with the arrangement of FIG. 6, the focusing of the image from the scintillation screen 20 may take place before or after it is reflected by the mirror 52, or may be focused by the mirror 52 itself. In addition, any of the optional elements previously discussed may be substituted into the arrangement of FIG. 5 or FIG. 7. This includes the x-ray absorbing screen 28, the anti-scatter grid, the fiber optic reducer 44, and the fiber optic faceplate 48.

A very effective, radiation dose-efficient approach for reducing x-ray scatter and increasing the dynamic range of electronically acquired x-ray images is the use of a slit-scan method. In this approach, a fan beam of x-rays is scanned over the patient and a linear array of detectors is used to detect the transmitted radiation. In typical applications the length of the detector restricts the width of the area that can be covered with one pass. Also, many small linear CCD or photodiode arrays are used to form a line of detection. This results in a rather complex detector assembly. If cooling of the detector assembly is required, it is difficult to accomplish for such an extended detector. Also, image intensification by using an electronic intensifier becomes difficult and very costly.

Figure 8:
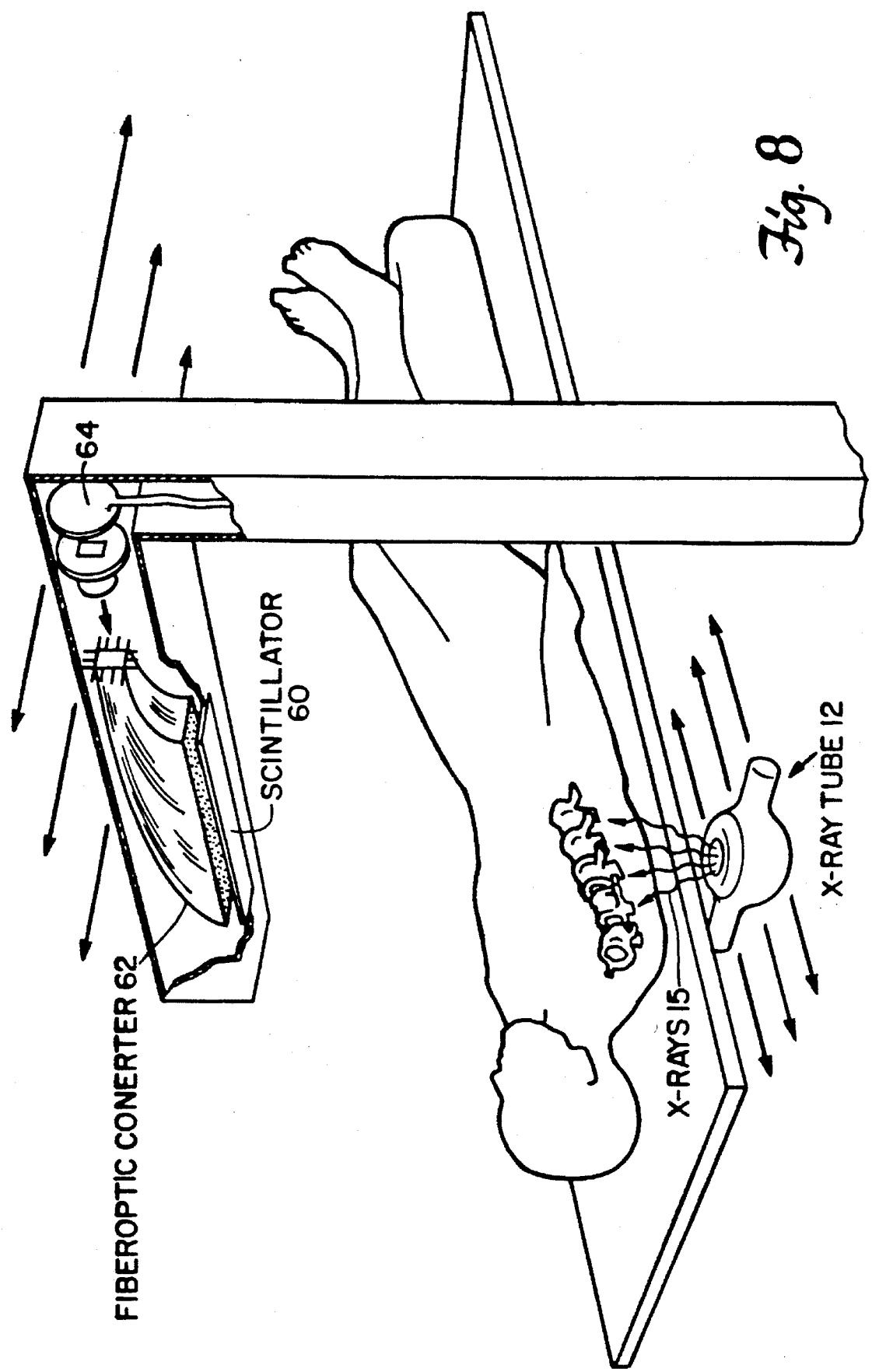
FIG. 8 is a perspective view of a scanning system of the present invention.

An alternative embodiment for dual energy bone densitometry takes advantage of the merits of slit-scan geometry without using a linear CCD or photodiode array. This approach is illustrated schematically in FIG. 8. An area CCD sensor 64 is used in conjunction with a line to area fiberoptic converter 62. This converter can be made of flexible or rigid optical fibers with cladding of lower index of refraction than the core material. As shown in FIG. 8, the CCD 64 is divided into a number of rows and a fiberoptic ribbon is optically coupled or bonded to each row. The coupling of the CCD 64 to the converter 62 can be accomplished using the various systems described in connection with other embodiments. An extramural absorber can be used to prevent light crossing from one fiber to another. The other ends of each ribbon are arranged in tandem to form a linear sensor. In front of the linear sensor (input end), an x-ray converting scintillator 60 is used such as gadolinium oxysulfide activated with terbium (GOS:Tb). Alternatively, a scintillating fiberoptic plate can be used for improved quantum efficiency at higher energies. A linear x-ray sensor with a very compact area detector is employed with the slit-scan embodiment.

A typical linear detector of this type comprises a few ribbons in tandem along the length of the slit, and from one to a multitude of ribbons across the width of the detector slit.

In a typical example, consider a 512×512 pixel CCD where each pixel has an area of 20×20 microns. A fiberoptic bundle with individual fibers of 60 microns in diameter is used for the embodiment. On the CCD each fiber will cover an area of approximately 3×3 pixels. Perfect alignment between each pixel and fiber is desirable but it is not essential for this application. Close packing of the fibers will result in an array of 170×170 or a total of 29,127 fibers covering the entire area of the CCD. Each ribbon of fibers corresponds to one row consisting of 170 fibers and covering approximately 512×3 pixels on the CCD. If all ribbons emerging from the CCD were arranged in tandem, the linear sensor would be approximately 175 cm in length. Alternatively, the ribbons can be arranged with a small number in tandem and a small number across the width of the slit. Using the above CCD, a 15.3 cm linear detector can be made with approximately 15 ribbons in tandem thus using only a small fraction of the CCD area.

Full use of the CCD area can be made by stacking the ribbons in groups of 15, (one ribbon per CCD row), thus creating a quasilinear detector consisting of an array of 2,550×11 fibers optically coupled to an x-ray scintillator. The dimensions of this slit detector will be 153×0.66 mm with a total sensing area of 1.0 $cm^2$. It is important to note that the total sensing area of the slit must be approximately equal to the total area of the CCD and the linear dimensions of the fiber optic output must be approximately the same as the linear dimensions of the CCD. A wider or longer slit will result in a larger area at the output end. In this case, a larger CCD can be used or a fiberoptic reducer optically bonded between the fiberoptic converter and the CCD. Alternatively, the converter itself can be tapered to match the size of the CCD. For higher spatial resolution the fiberoptic converter is made with optical fibers of smaller diameter (5–6 microns).

If higher signal amplification is required for some high detail low dose applications, a proximity focused image intensifier can be optically bonded between the fiberoptic taper and CCD or between the fiberoptic converter and fiberoptic taper. The image intensifier can be a proximity diode type or a microchannel plate device, both commercially available. Alternatively, an integral assembly of CCD and intensifier can be used commonly called an "intensified CCD". Another approach is to use a lens coupling between the output surface of the fiberoptic converter and the intensified or non-intensified CCD.

Cooling of the CCD can be accomplished easily by a thermoelectric cooler. Cooling is required only when Very high contrast resolution is required and the image acquisition time is relatively long. If the CCD is read out at 500 kHz ($5\times10^5$ pixels/sec), an area of 150 mm×150 mm of the subject can be scanned in approximately 114 seconds (approximately 2 minutes). Faster scanning is attainable by increasing the readout rate of the CCD.

Figure 10:
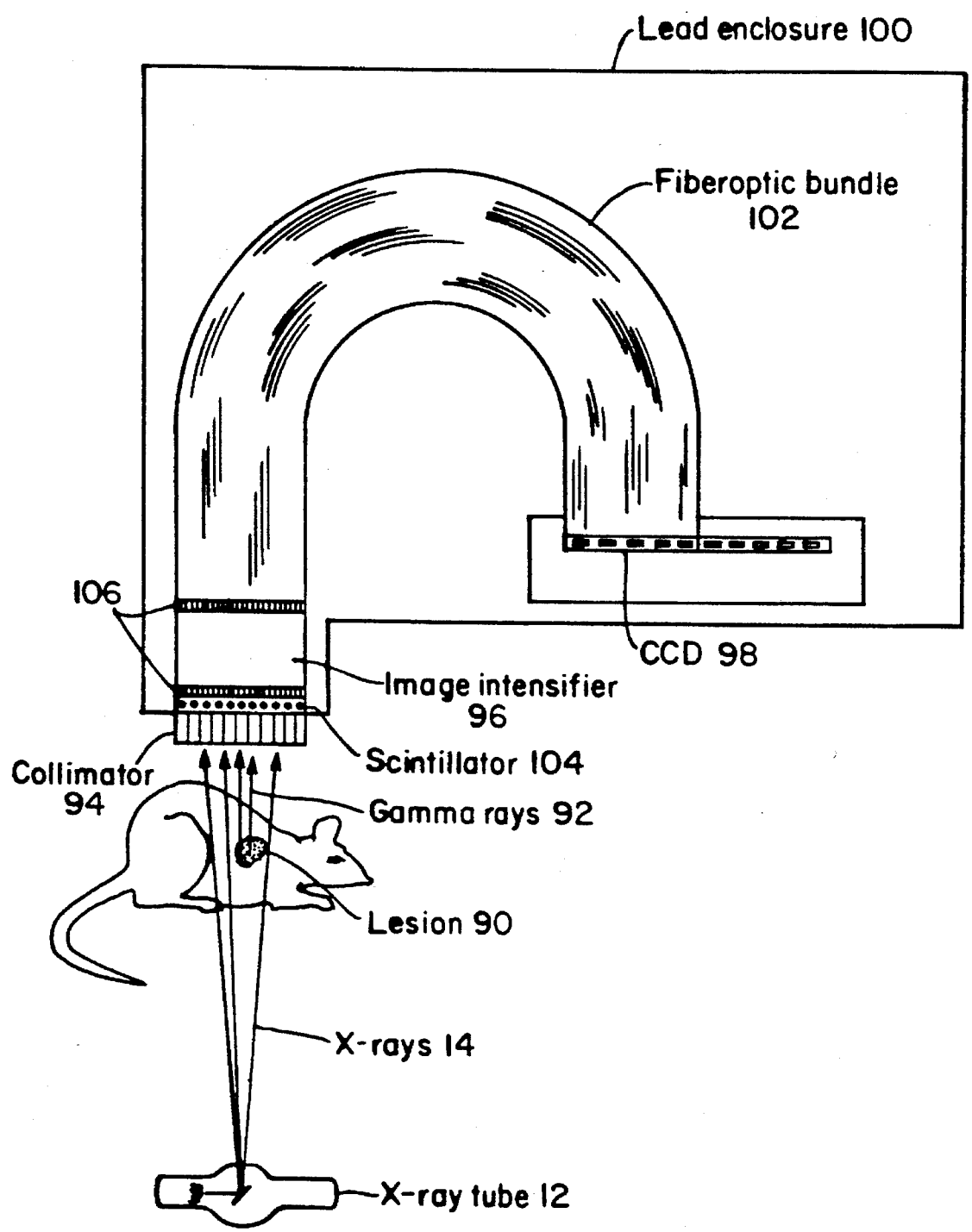
FIG. 10 is a schematic sectional view illustrating a frame transfer CCD used for both emission and transmission studies.

Alternatively, a frame transfer CCD such as the one illustrated in FIG. 10 can be used for faster scanning. This device uses one half of its sensing area for storage and not for sensing. In this way the transfer of the image from the sensing area 91 to the storage area 93 is accomplished in a few milliseconds. A smaller CCD such as a 128×128 or a 64×64 element could be used for this purpose in a similar arrangement as with the 512×512 CCD. Also, larger area CCDs can be used for this purpose. Pixel binning as described previously can be applied in this detection approach. A Gadolinium-153 (Gd-153) radiation source can be used as described in previous sections in place of an x-ray tube. The Gd-153 source is a small pellet or a collimated line source parallel with the long dimension of the detector.

The line to area conversion design enables us to remove the CCD from the direct path of the x-ray beam, thus it allows for easy shielding of the CCD from direct x-ray interactions. This prolongs the useful life of the CCD and it alleviates the "snow" effect which results from direct interactions of x-rays with the sensor. Moreover, this approach allows for greater light transport efficiency between the scintillator and CCD than lenses or fiberoptic tapers. Note that the pixel binning approach enables the operator to select the desired spatial resolution and contrast without any mechanical modifications on either the x-ray beam or the detector collimator. The pixel size of the detector which determines resolution and contrast can be controlled by a command from the computer. This x-ray imaging modality can be used very effectively to optimize the scan depending on patient size, and medical history.

An alternate approach provides an improved rectilinear scanning method for quantitative x-ray radiography. In this embodiment, a two dimensional CCD optically coupled to a scintillator is used as the detector of x-rays in a rectilinear scanning mode. The CCD may be a full frame or a frame transfer device. The frame transfer CCD will enable faster data scanning and acquisition.

The CCD scintillator assembly is extremely critical to the performance of the system. Direct optical bonding of a polycrystalline scintillator such as gadolinium oxysulfide with the CCD is possible but this approach is not efficient in shielding the CCD from direct x-ray interactions. If the thickness of the layer is increased the spatial resolution of the x-ray images degrades due to light diffusion. The use of a scintillating fiberoptic plate between the polycrystalline scintillator and the CCD provides a solution to this problem.

A scintillating fiberoptic plate is a fiberoptic faceplate designed to convert x-rays or U.V. light into green light with peak emission at about 550 nm. This faceplate is manufactured with extra mural absorber to prevent light diffusion between individual fibers. The area of the scintillating fiberoptic plate must cover the CCD completely. The desirable thickness depends on the energy of the x-ray radiation. A thickness of 5 to 10 mm is preferable but a thinner or thicker plate can be used. The use of a very thick scintillating fiberoptic plage such as 10 mm or 20 mm will eliminate virtually any undesirable direct x-ray interactions with the CCD. The scintillating fiberoptic plate can also be used without the thin layer phosphor. However, the combination of the two will produce better image quality at a reduced radiation dose to the patient. Alternatively a conventional fiberoptic plate can be used as a substrate to the scintillating fiberoptic plate. The optical coupling of the polycrystalline phosphor on the fiberoptic can be accomplished by direct deposition techniques or by using an optical adhesive.

In an alternate approach, a bent fiberoptic bundle can be used between the scintillator and the CCD. The geometry of the bent bundle allows for extremely effective shielding of the CCD from extraneous x-ray radiation. A lens coupling between the CCD and the fiberoptic converter can also be used. For improved sensitivity, a proximity focused image intensifier, an image diode or microchannel plate can be used at the input end of the fiberoptic or between the fiberoptic bundle and the CCD. A preferred approach is to use the intensifier at the input end. A scintillator can be optically bonded to the input of the intensifier or an intensifier with a scintillating fiberoptic input plate can be used.

The x-ray tube is aligned in a C-arm configuration with the detector. The x-ray beam is approximately congruent with the area of the detector which is approximately 1×1 cm at the detector plane. As x-rays are transmitted through the patient, some (20%–60%) are absorbed by the primary polycrystalline scintillator producing visible light. This light is transmitted through the optically transparent fiberoptic faceplate in the direction of the CCD. The x-rays not interacting with the primary scintillator will be absorbed by the fiberoptic faceplate. If a scintillating fiberoptic faceplate is used, these x-rays will be absorbed in the fibers thus producing additional scintillations. Therefore, the scintillating fiberoptic plate acts as a light conduction device, x-ray shield, secondary x-ray detector and an an x-ray signal amplifier.

Upon interaction of the x-ray induced light with the photosensitive surface of the CCD an electron charge is generated which is proportional to the number of x-ray interactions in the scintillators. The cumulated charge on the CCD is then read out. However, in this rectilinear scanning mode, each CCD readout will correspond to a small segment of the total image, approximately one square centimeter. Therefore, the entire image is acquired by spatial additional of each image segment. For example, if a 15×15 cm field is covered and the sensor area is 1.0×1.0 cm, $15^2$ (225) segments must be acquired and synthesized. A 512×512 pixel CCD operating at 500 kHz will read out each segment in 0.5 seconds and will require about 2 minutes for the entire scan at a scan speed of about 2 cm/sec. Faster scanning is attainable by increasing both the scanning speed and the readout rate of the CCD.

A dual-energy scan will be acquired by first scanning the entire area at high tube potential, typically 130 kVp without binning and then repeating the scan at low tube potential, typically at about 70 kVp with binning. An automatic slide mechanism places high aluminum filtration for the high energy beam and less filtration for the low energy beam as described previously. The images of each energy level are stored in the computer for subsequent dual photon analysis. Pixel binned acquisition will be possible at both energies for improved precision. Where both high and low energy images are identically binned, this produces an exact correlation between the images produced. A third high energy-high resolution image can then be used to define the outline of the object being scanned. Note that a gadolinium isotope source with a shutter can be used.

Alternatively, the energy level of the tube can be switched from low to high for each segment of the acquisition and each segment representing high and low energy is stored for subsequent analysis.

An alternate approach employs light intensification from the screen to the CCD sensor. In this approach, an electrostatically focused image intensifier 2 (In FIG. 2) is employed as the primary detector in place of the scintillating plate. This intensifier preferably employs Cesium iodide input phosphor with an approximate diameter of 15 cm and thickness of 0.3–0.5 mm. The high voltage of the image intensifier tube can be reduced to approximately half the normal value. A reduction in the image intensifier accelerating potential will contribute to an improvement in the image contrast characteristics and dynamic range of the device. The CCD sensor is optically coupled to the output phosphor of the image intensifier by a fast lens with an f-number of about 1:1.0. Due to the high signal intensification, cooling of the CCD is not essential but it can be applied if very low thermal noise levels are desirable. The use of an intensifier allows for the use of a CCD with lower noise performance characteristics, thus lowering the cost and complexity of the instrument.

Ideally, the detected signal is produced by x-rays that have been transmitted through the body without any scatter interaction. Detection of large amount of scatter events will result in non-linearities and in a reduction in the dynamic range. Effective supression of scatter is accomplished by using a small field of view, typically 10 cm×10 cm and by using a air gap (approximately 20 cm) between the patient and the scintillating plate. Alternatively a small field of view can be used in conjunction with a linear or crossed antiscatter grid.

Figure 9:
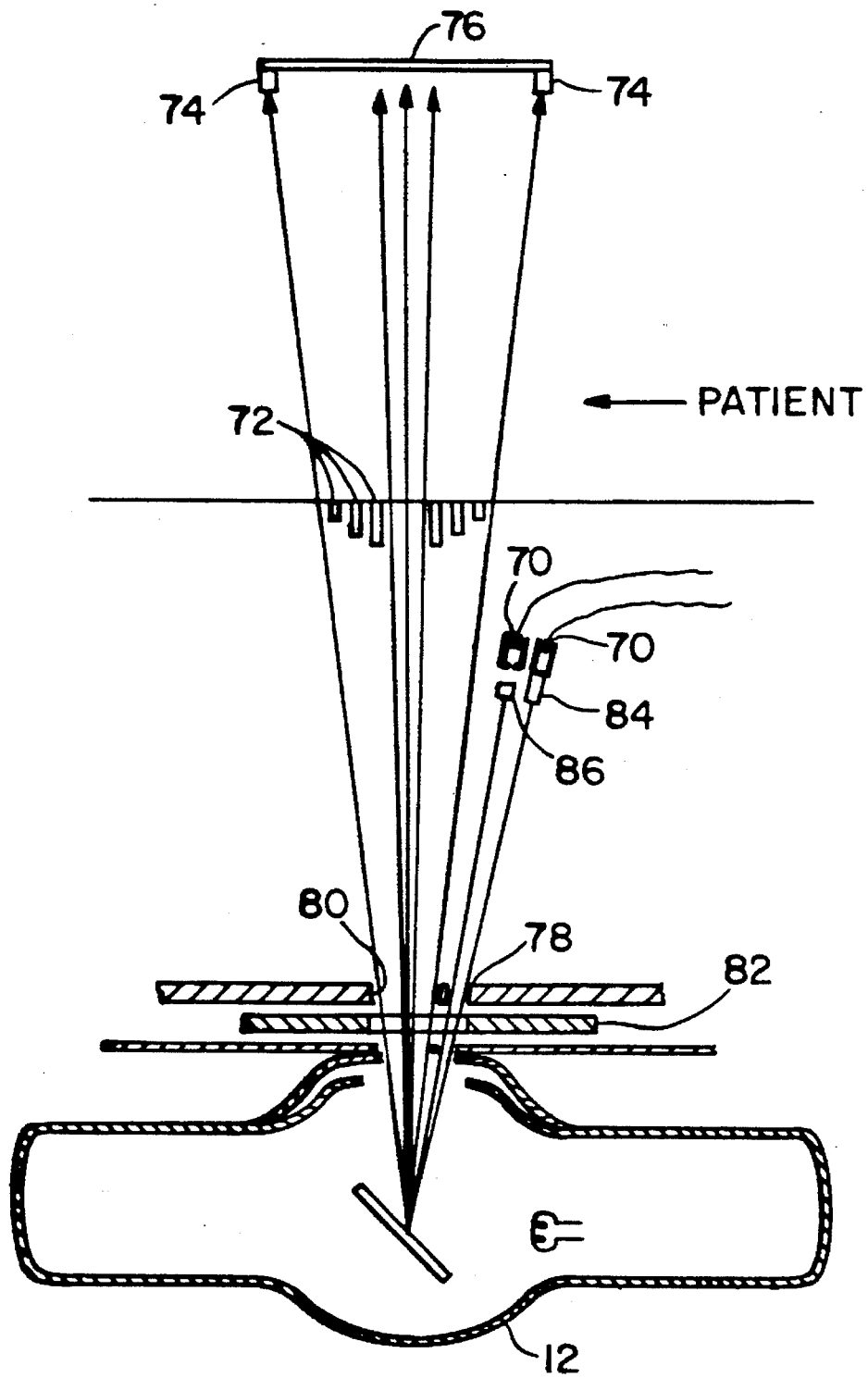
FIG. 9 is a schematic sectional view illustrating the sensor control system.

An internal instrument stability control system has been incorporated to provide a means of automatic compensation for any instabilities in the x-ray tube potential and current. The stability control device is not essential for the operation of any of the described techniques but it provides better reliability and precision in the measurement of bone density. A schematic representation of the proposed device is shown in FIG. 9. The output of the x-ray tube 12 is monitored by a pair of x-ray sensors 70 placed at a secondary x-ray beam port 78 adjacent to the main beam port 80 near the tube window. The sensors can be silicon diodes, cadmium telluride radiation sensors or any other solid state x-ray sensor. Alternatively, a pair of compact photomultiplier-scintillators or a photodiode scintillator assembly could be used. Both detectors operate in the charge integration mode and the detected signal is continuously monitored as a function of time during the entire scan for each energy. This time varying signal is digitized and stored in the computer memory. The change in the filtration of the secondary beam with energy is identical to that in the main beam because it is controlled by the same filter changing mechanism. As described further in connection with FIG. 12 the sensor system can be used to normalized the detected information or to control operation of the x-ray source to prevent or reduce unwanted variations in the source output.

In front of one of the sensors 70 an amount of polymethyl methacrylate 86 is placed to simulate an average thickness of soft tissue. In front of other sensor 70 an amount of bone simulating material 84 is placed in an amount equivalent to that encountered in the spine or femur. Various hydroxy apatite-epoxy mixtures are commercially available for bone simulation in x-ray imaging. Therefore, a secondary detection system with a bone standard of known density and a soft tissue equivalent thickness is provided in this embodiment.

The signals from each sensor 70 can be used to compute the density of the bone internal standard as a function of time during the scan. Any deviations from a constant density of this standard are due to changes in either the energy or intensity of the x-ray emission. Each value of bone density computed in the patient scan corresponds to a computed value of the bone standard. Therefore, each computation of bone density derived from a pair of high and low energy CCD frame acquisitions can be corrected or normalized by using the deviation from the density of the internal standard. For example, if the value of the bone standard during the rectilinear scan deviated by plus 3% in a given area of the image, the computed bone density of the patient scan must be corrected by that amount in this area. This internal reference approach can be used with all stationary and scanning embodiments described herein.

In conjunction with the above calibration approach, a number of strips 72 (square rods) of bone simulating epoxy material, or aluminum of equivalent x-ray absorption are placed under the table 73 which run in the direction of the scan for the slit scan approach. Each linear strip has a different thickness or bone equivalent density. As the x-ray tube and detector assembly is scanned over the area to be tested, each set of rods are scanned and their density computed. The consistency of the measured densities of these rods is used to ensure proper operation of the system. This set of standards can be placed anywhere from the x-ray exit port 80 to the edges 74 of the detector 76.

The imaging of radionuclide distributions in biological tissues or specimens is a routine task performed in virtually all biomedical research laboratories by the well established technique of autoradiography. In this procedure, a thin slice of a specimen is placed in contact with photographic film thus allowing the radiation from the specimen to expose the film. Subsequently, the film is processed by standard chemical development techniques, manually, or by using an automatic processor. Frequently, an intensifying screen is used in order to enhance the absorption efficiency of the image receptor and for a reduction in exposure time. Intensifying screens are especially useful when images of relatively high-energy gamma or x-ray emissions are recorded (20–200) keV. Also they can be useful for high energy electrons.

Autoradiography produces images reflecting the biodistribution of a radionuclide and it has been established as a powerful tool in many biomedical disciplines. Its major shortcomings relate to problems with quantitation of the relative or absolute concentration of radionuclide in an area of interest. This difficulty arises from the non-linearity of photographic film typically used and in reciprocity law failure when intensifying screens are used. Moreover, the development temperature, and in general, the condition of the processing chemicals have an influence on the film fog level and contrast. All these factors render quantitation a very difficult and time consuming task which becomes vulnerable to many uncertainties in quantitative autoradiography. Despite these problem, several investigators have digitized film autoradioigraphs by using microdensitometers or video cameras for both quantitation and image enhancement.

In autoradiography, the image represents areas where the radiotracer has been extracted. The anatomical information on the original tissue slide is not transferred with great detail in the autoradiograph. For proper interpretation, it is necessary to observe the tissue slide and autoradiograph side by side in order to correlate radiotracer distribution with anatomy. Often it is necessary to superimpose the slide with the autoradiograph in order to identify the exact anatomic location of the radiotracer. In this process the accuracy in assigning an anatomic location to the tracer is severly compromised.

One of the most important problems with autoradiography is the long period of time required in order to expose the film. In most applications this time ranges from a few hours to several days, even weeks in some cases. Therefore, the technician may have to wait for a few days in order to find out whether an exposure has to be repeated.

Autoradiography does not relate to in vivo imaging of radionuclide distributions in humans or animals. Rather it relates to detecting radioactive distributions in excised samples. All available film-screen image receptors have extremely low quantum efficiencies for most gamma emitters commonly used for this purpose. Moreover, the presence of a large volume of tissue results in enormous amount of gamma ray scatter which will reach the image receptor and degrade the contrast and spatial resolution. The film-screen receptors do not have energy discrimination capabilities, therefore scattered events cannot be rejected. The use of a collimator to suppress scatter will result in a dramatic reduction in geometric efficiency.

Thus the present invention, in its various embodiments, provides an effective means for performing autoradiography by providing a compact device that performs the data acquisition for autoradiography quickly and can superimpose both emission and transmission studies to correlate the emission image with the anatomical features of the object under examination. The embodiments described in connection with FIGS. 10 and 11 below can be used to perform autoradiographic procedures.

Radionuclide imaging of humans and animals is performed on a routine basis by using the Anger camera, most commonly refered to as a "Gamma Camera". The gamma camera has a quantum efficiency in excess of 50% for the most commonly used radionuclides and it has the capability of discriminating scatter from primary photons by pulse-height analysis of each detected photon. The intrinsic spatial resolution of the gamma camera is approximately 3.5 mm. The total spatial resolution of the camera, including the degradation due to its collimator, can vary from 5 mm to 12 mm. Modern gamma cameras can detect photons at the rate of 25,000 counts per second (cps) without significant dead time losses. At higher count rates, significant deviations are observed between true and detected events. This is due to limitations inherent in the design of both the detector assembly and processing electronics.

The following presents a further embodiment relating to imaging of radionuclide distributions in tissue samples and in vivo quantitative imaging of humans and animals. This procedure employs a charge-coupled device to detect and process information to provide, in essence, a compact "gamma camera" using a highly sensitive stationary (or scanning) detector to conduct both emission and transmission studies at count rates up to $10^6$ of the object being examined.

Existing gamma cameras have limited spatial resolution, limited capability to perform in high count-rate conditions and it cannot be used to record x-ray transmission (radiographic) images with any degree of acceptable detail to satisfy radiographic imaging standards. Therefore, the recording of a high quality radionuclide (physiologic) image and a radiographic (anatomic) image with the same detector for accurate correlation of the physiologic and anatomic image remain difficult. Where very high detail is necessary, the gamma camera is generally not capable of producing better than 5 mm resolution even under the most favorable conditions. Therefore, the imaging of small parts of the body or imaging small animals like mice cannot be performed with any reasonable detail using the gamma camera. This also applies for the imaging of tissues containing radioactive materials.

The following procedures enable the acquisition of high detail radionuclide images and the option of combining them with the x-ray radiographic images with the same detector.

This approach employs a novel acquisition scheme that enables imaging spectroscopy of gamma rays, x-rays or nuclear particles by using a CCD. CCDs have been employed in the past without a scintillator for imaging spectroscopy of very soft x-rays, up to the energy levels of about 6–9 keV. However, above this energy, the CCD becomes virtually transparent to x-rays or gamma-rays. Generally, scintillators have not been used in conjunction with a CCD for imaging spectroscopy because it is believed that the conversion from gamma-rays to light will destroy the useful information carried by the interacting gamma-ray or x-ray. Therefore, imaging spectroscopy of gamma-rays or x-rays in the energy range of about 10 keV to 2,000 keV with a CCD has not been explored. Also, alternating the mode of operation from a counting, energy sensing detector to an integrating detector for radionuclide and radiography, respectively, presents a useful procedure for imaging spectroscopy. Note, however, that the counting procedure can also be used in certain x-ray transmission measurements to measure the energy thereof.

When light interacts with the sensitive surface of the CCD, it generates a charge which remains stored in the pixel where this interaction occurred. As with previous embodiments the magnitude of the charge is directly proportional to the detected intensity of light. Each pixel is represented by its two-dimensional coordinates and by an intensity value. The energy required to produce an electron in the sensitive silicon surface of the CCD is about 3.65 eV.

This value enables the determination of the energy of detected photons if the system can either detect one photon at a time, or if the number of the photons detected per pixel is known. This provides for imaging of radionuclide distributions with a simultaneous measurement of the energy of the detected events. This procedure is termed "Imaging Spectroscopy" and provides a technique using gamma rays, beta-rays, and x-rays in conjunction with CCD technology.

The upper energy limit of soft x-ray imaging is between 5–10 keV. At 10 keV, the quantum efficiency of a CCD is approximately 5% and it diminishes rapidly at higher energies. The small fraction of the total number of events interacting with the CCD will result in a high partial energy transfer to the sensor with losses in proportion with the energy and the signal. Therefore, when the CCD is used as the primary detector of high energy photons or particles, it is virtually unusable for performing imaging spectroscopy. The following procedure provides high resolution imaging spectroscopy using a CCD that is suitable for many applications including position emission tomography and nuclear particle imaging.

A schematic of the device is shown in FIG. 10. An important component of this device is a CCD 98 with low readout noise, high charge transfer efficiency and dark current levels. A CCD with less than 10 electrons/pixel (rms) readout noise is suitable for this purpose. The dark current can be reduced to less than 0.6 electrons/sec at −40 C. by a compact thermoelectric cooler.

In one embodiment of this method, a thin scintillator 104 is used as the primary detector of x-rays. One such scintillator can be a layer of gadolynium oxysulfide or thallium activated cesium iodide or any of the commonly available phosphors. The scintillator 104 is bonded to a fiberoptic faceplate 106 and the faceplate is bonded to an image intensifier 96. The intensifier is bonded to a second faceplate 106 that is bonded to bundle 102. Optical bonding of this type is a well established. To further illustrate this embodiment the sensitive area of the scintillator 104, faceplates 106, image intensifier 96, fiberoptic coupler 102, and CCD 98 have identical dimensions. Note that a collimator 94 can be mounted on the lead enclosure 100 and is used during the transmission study, and depending on its configuration, can also be used during the emission study. Note that the collimator 94 can optionally be removed during emission studies.

When an x-ray photon within the rays 14 interacts with the scintillator 104, it produces light with intensity which is proportional to the energy of the x-ray. This light is transported through the fiberoptic faceplate 106 and interacts with the CCD 98. The interaction of optical photons in each CCD pixel will produce a number of electrons in direct proportion to the number of optical photons and to the energy of the detected x-rays 14 or gamma-rays 92 that are produced by the isotope that has collected in the lesion 90. Isotopes commonly utilized include TC 99 m or I-125. The following example as a first order approximation of the expected energy resolution from the detector.

A 60 keV x-ray interacts with the scintillator resulting in 3000 optical photons. Approximately one half of these photons are emitted in the direction of the CCD. Assuming a Lambertian distribution of the emitted photons from the screen, the transmission through the fiberoptic plate is approximately 40%. Therefore, 600 optical photons will be arriving at the CCD. The quantum efficiency of the CCD is approximately 40%, therefore only 240 photons will be detected in one pixel.

It can be shown that the energy resolution can be in the order of 10% which is approximately twice that attained with conventional NaI-crystal spectrometers at this gamma-ray energy.

Figure 11:
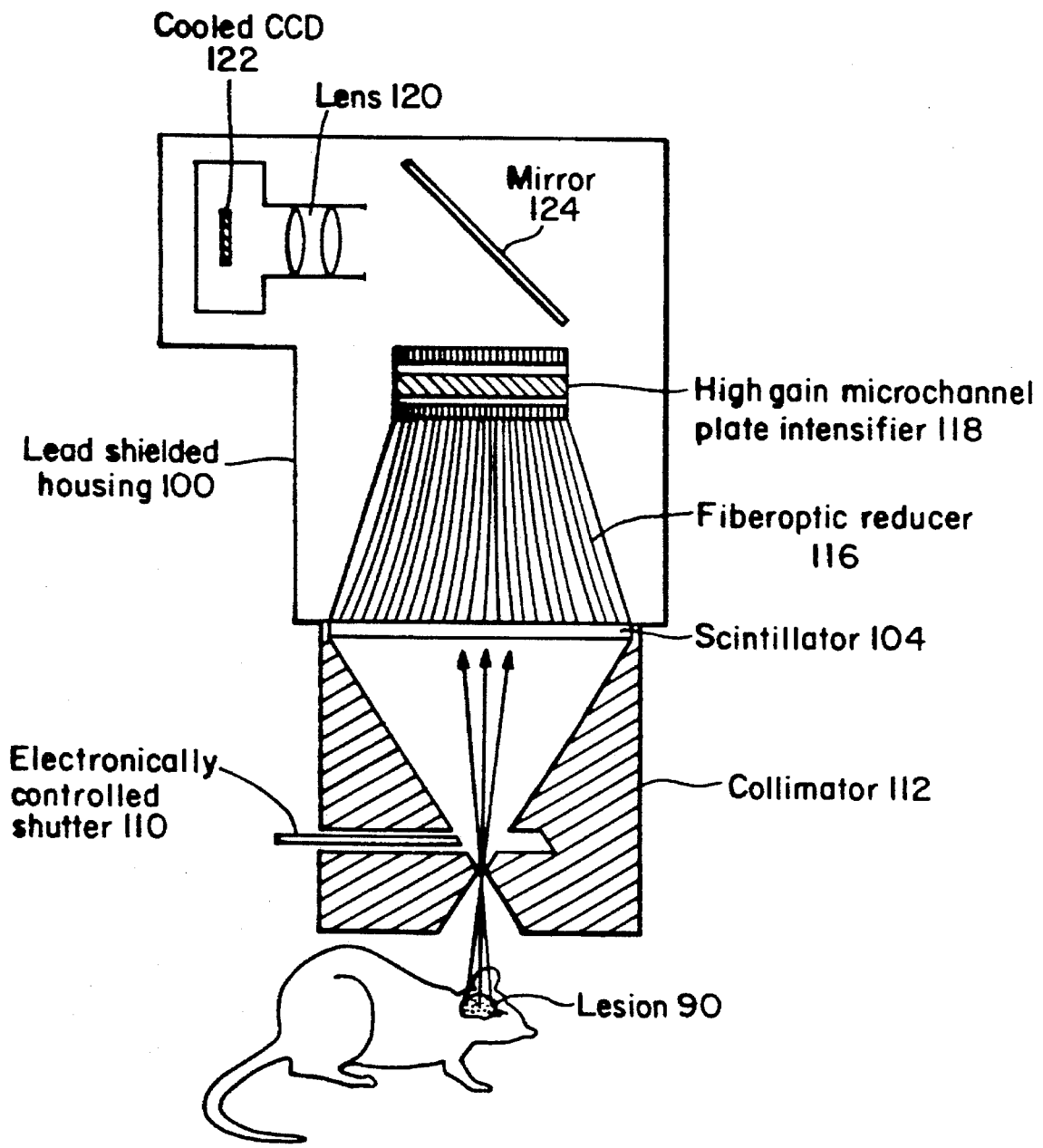
FIG. 11 is a schematic sectional view of a CCD imaging system for both emission and transmission studies.

FIG. 11 depicts an alternative embodiment in which a "pin hole" collimator 112 with shutter 110 is used in performing an emission study of lesion 90 or any selected organ. The emission from the lesion or organ impacts the scintillator 104, into housing 100, through the fiberoptic reducer 116, coupled to the intensifier 118, and than directed off mirror 124, lens system 120, and onto a cooled CCD 120.

This procedure produces radionuclide scintigraphy with spatial resolution in the order of about 1 millimeter or less, and transmission images with resolution in the order of 0.2 millimeters. The spatial resolution and sensitivity of the detector will be selectable for both emission and transmission modes via pixel binning. The detector operation will be selectable for pulse-height analysis or integration. For x-ray transmission imaging, the integrating mode of operation is preferred. Note that during x-ray transmission imaging, the pin hole collimator will be removed. Emission imaging of thick tissues requires a collimator, either a multihole type or a pinhole collimator. Very thin specimens can be imaged without a collimator by placing them very close to the scintillator.

This camera has the capability of detecting very high count rates. In conventional gamma cameras, each x-ray photon interaction occupies the entire scintillator and electronics for a period of time of 1 to 8 microseconds after it is detected. In the present method, due to the multiple detectors, higher count rates can be handled due to the multiple detectors, and higher count rates can be handled without using a scintillator with short decay time. Count rates up to $10^6$ counts per second can be acquired with very low probability (less than 1%) of detecting 2 gamma ray events in one pixel when operating in the pulse-height analysis mode.

Note the scintilator can be bonded directly on the fiberoptic bundle without the use of an image intensifier. Also, the scintillator can be bonded directly on the CCD without the use of a fiberoptic bundle. A frame transfer CCD is a preferred approach, but a full frame CCD can be used.

The following "shutter" methods can be used (a) a frame transfer CCD; (b) a gated image diode, or microchannel intensifier; or (c) a liquid crystal shutter with very thin window or fiberoptic window. The liquid crystal shutter can be positioned between the fiberoptic bundle and the scintillator.

Note that the system has applications for small animal imaging, skeletal imaging, monitoring of fracture healing, thyroid scintigraphy, Bremsstrahlung imaging of beta emitters within the body (radiation synovectomy), intraoperative imaging probe, radionuclide angiography, small parts imaging, and pediatric nuclear imaging.

Figure 12:
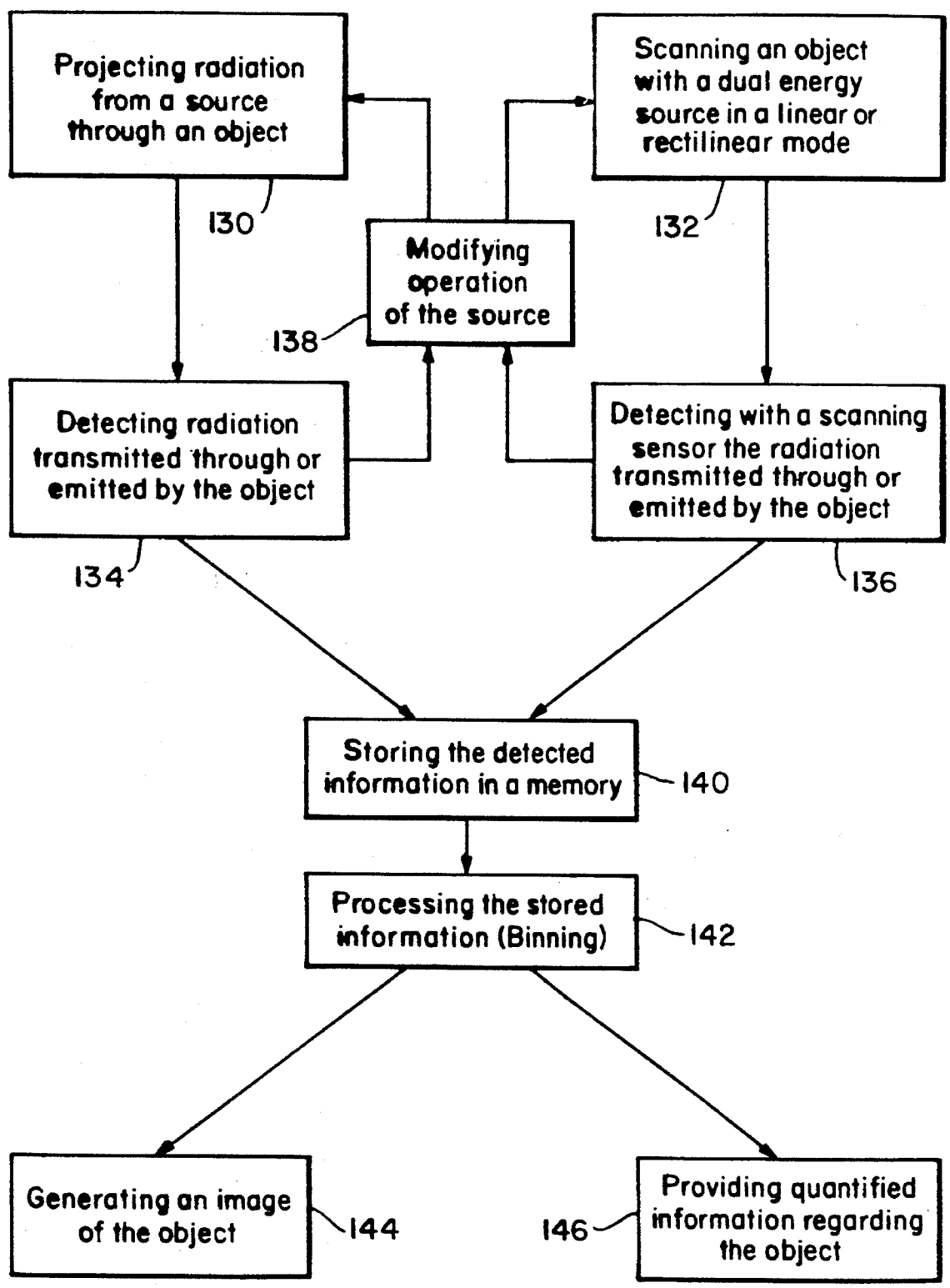
FIG. 12 illustrating a process flow sequence that is used in performing the imaging methods of the present invention.

FIG. 12 illustrates in schematic form several methods that can be used in performing quantitative imaging in accordance with the various embodiments of the invention.

Note that one can use either a stationary source and detector to project radiation 130, or a scanning source and detector assembly to scan the object being examined 132.

Both stationary and scanning embodiments utilize a CCD detector that transfers the detected information to a memory 140. The information can be binned or processed 142 to accomplish various tasks. This processing can include the application of software modules to correct for non-uniformities in the source or collection components, or to identify events where light from one gamma-ray interaction has spread to a number of neighboring pixels. Clusters of pixels with high intensity can be identified as primary events and low intensity clusters can be identified as scattered radiation and be eliminated by a filter.

Quantified information such as an intensity histogram (i.e. a pulse height spectrum) can be generated 146 and a display of the object can be generated 144 with the unwanted pixels removed.

After each set of data is produced in both the stationary and scanning embodiments, the conditions for operation can be modified 138 to produce an image at a different energy level, to perform an emission or transmission study, or to rotate the source and detector assembly relative to the object under study to produce three dimensional images or two dimensional images at different angles.

The emission and transmission studies can be displayed alone or superimposed. Due to the binning capability of the system a one to one correspondence exists between both emission and transmission images that was previously not possible. This high resolution image can be color coded to distinguish between the emission and transmission images.

Figure 13:
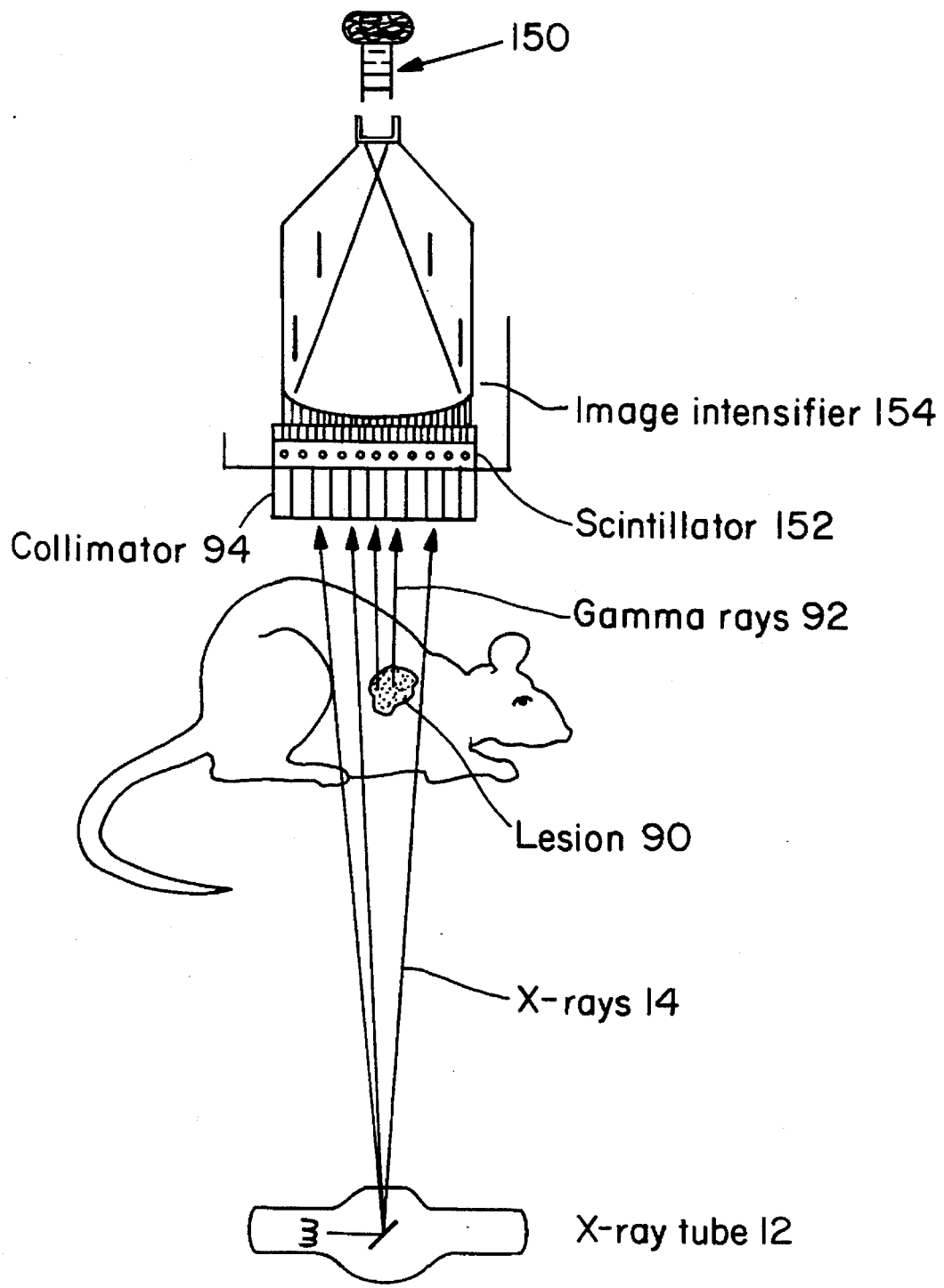
FIG. 13 is an alternate embodiment of a CCD imaging system that can be employed for both emission and transmission studies.

Another preferred embodiment is illustrated in FIG. 13 where a full frame or frame transfer cooled CCD 150 with a transparent scintillator 152 bonded on the sensitive surface of the CCD, or to an image intensifier 154, as shown. The scintillator 152 is preferably emitting anywhere from the UV blue to the red regions of the spectrum upon stimulation with x-rays or gamma-rays. The preferred scintillator is one emitting in the green such as CsI(TI) or Cadmium tungstate, or alternatively a gadolinium based ceramic scintillator available from Hitachi corporation. This scintillator has about twice the density of sodium iodide or CsI(TI) and has higher efficiency. A fiberoptic plate (straight or reducing) can be incorporated between the CCD and scintillator. Alternatively, an electrostatic image intensifier 154, or image diode intensifier, can be incorporated between the scintillator and the fiberoptic plate. The scintillator 152 can be optically transparent plate or comprise a fiberoptic array with fibers ranging in diameter from 0.006 mm to one or more millimeters. The thickness of the plate can be in the order of 0.5 mm to 5 mm.

Another preferred embodiment employs a CCD of the type described above but in conjunction with an electrostatic demagnifying image intensifier. The optical coupling of the CCD is accomplished by a fast lens at the output end of the image intensifier or by a fiberoptic plate between the output screen and the CCD.

The process of obtaining a desired image includes the initiation of acquisition with the CCD for about one second or at a desired binning configuration, typically coarser than 2×2 pixels. Shorter acquisition time will be required for high count-rates and longer acquisition time is tolerated for low count rates. The optimal acquisition time for a particular application can be determined empirically by acquiring a few test frames and search for coincident events within individual pixels. Very short acquisition times (less than 1 millisecond) are easily attainable by using a fast mechanical shutter, an electrooptical shutter, or by gating the image intensifier tube. This enables acquisition with spectroscopy capability even at very high count-rates. Each acquisition "frame" will record from a few hundred to a few thousand counts. After acquisition, each frame is stored in the computer memory for subsequent processing. Depending on the application, the total number of frames for a complete acquisition can vary, for example, from ten to a few hundred.

Each gamma-ray event in a given frame stored in the computer is represented by its x and y coordinates and by an intensity value (z) which is the number of electrons generated in this area of the CCD. The z value is directly proportional to the energy of the gamma ray (or x-ray). The number of electrons generated from each interaction should be confined to one pixel or group of binned pixels forming a "superpixel". In a significant percentage of interactions, the electrons generated from a single gamma-ray interaction can be split between two or three pixels or superpixels. These split events form clusters in the image matrix which can be easily identified by the computer software and assigned an x and y coordinate.

Figure 14A:
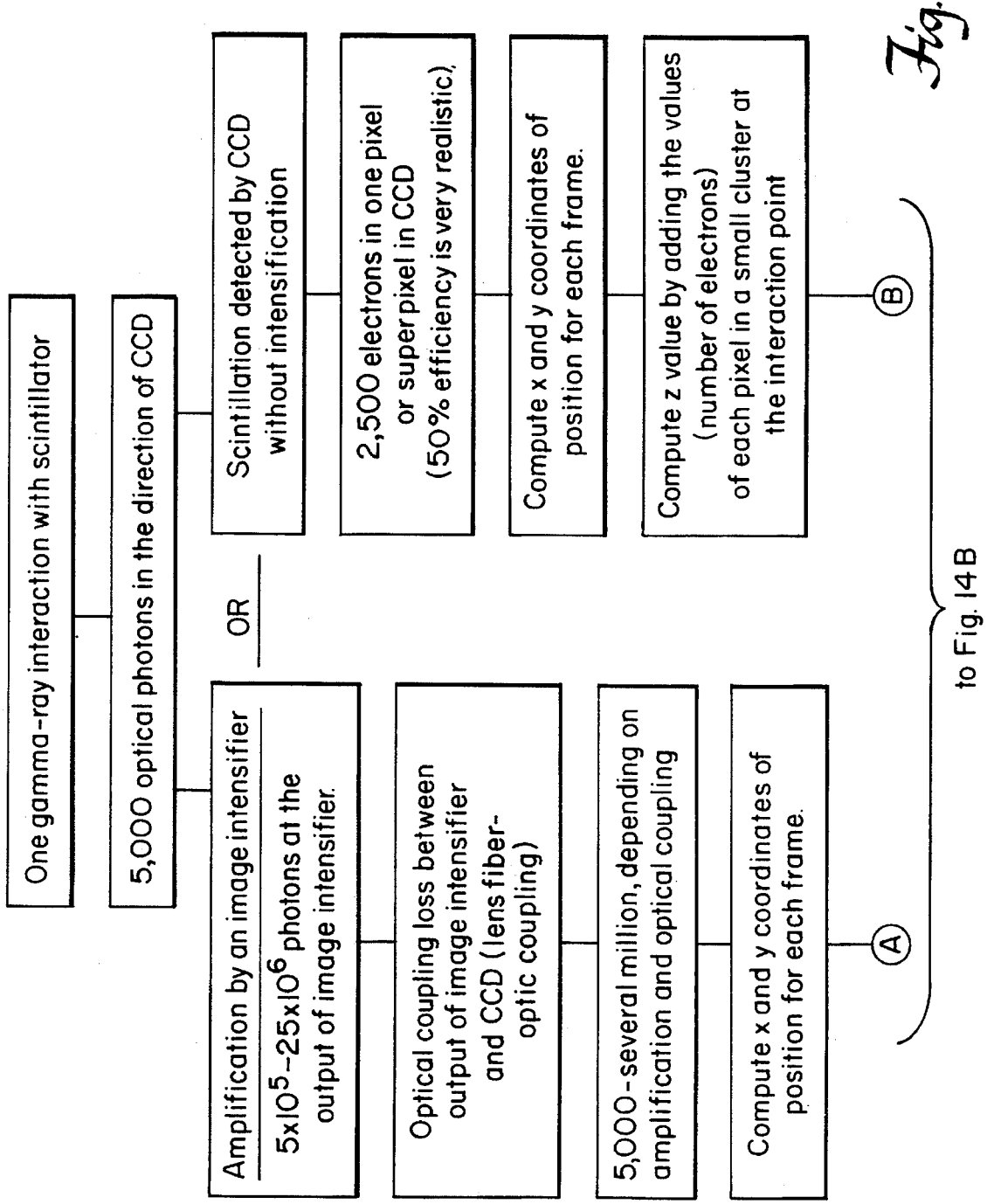
FIGS. 14a and 14b illustrate a process flow sequence for conducting emission and transmission studies of tissue.
Figure 14B:
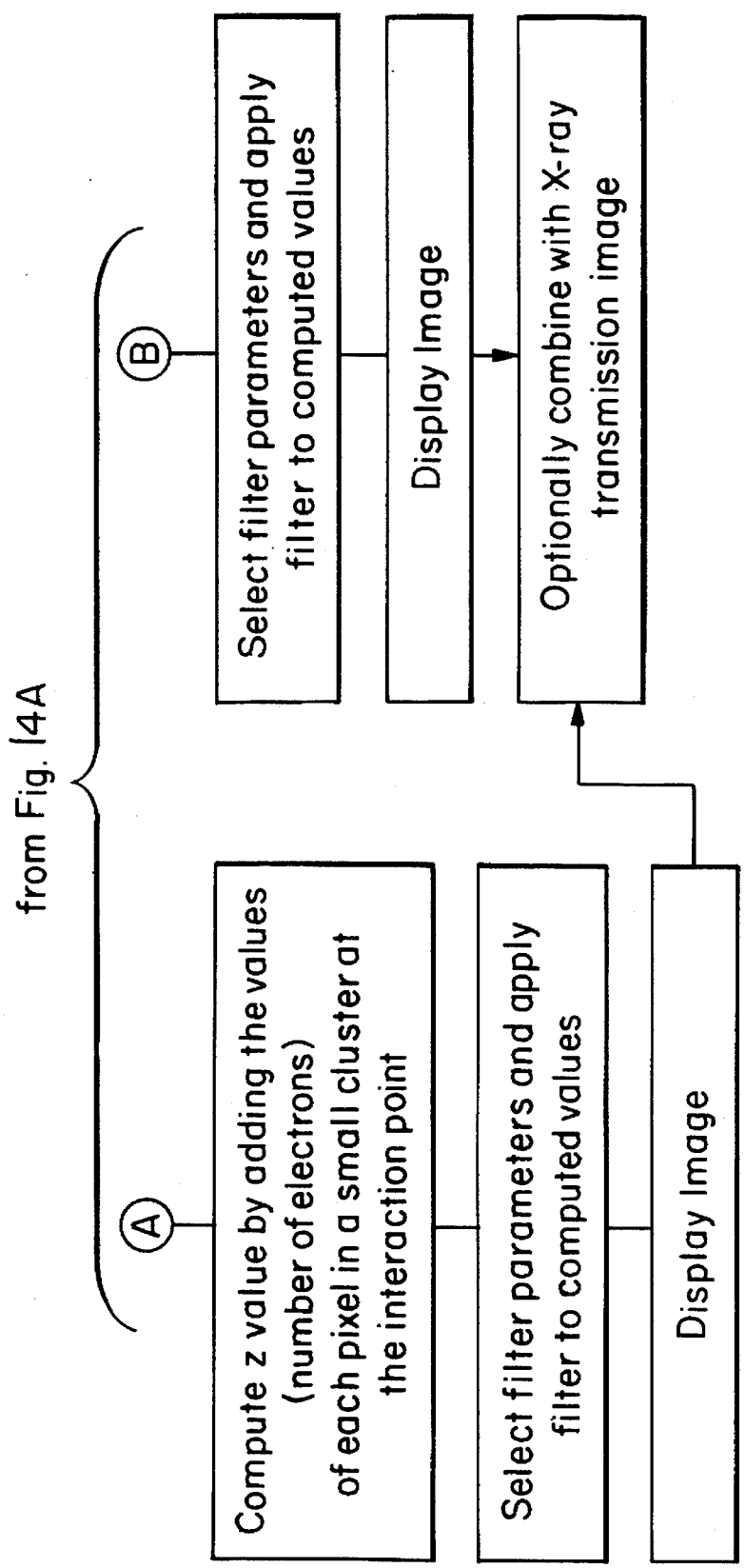

In one embodiment, as shown in the process flow sequences of FIG. 14, pulse height analysis uses the value of these neighboring pixels which are summed to produce the z value for this gamma-ray event. Low z values represent gamma-rays which have been scattered and have lost a portion of their energy. These events are generally not desirable for inclusion in an image because they carry false position information. Therefore, the degree of rejection of each event can be decided by software on the basis of the z value and a spectrum of the number of gamma-rays versus the z value (energy) can be recorded. This filtering process can be repeated for each frame and all the frames can be added together to form the final image. The operator can optionally go back to each original frame, use a different z value threshold and reconstruct the final image using different filter parameters. Variations in the sensitivity of each pixel or superpixel can be mapped and included in the computer for pixel by pixel corrections. The ability to discriminate different radiation sources measured simultaneously or sequentially includes defining filter parameters as selected energy threshold values or ranges.

In this radionuclide imaging technique, the degree of scatter rejection can be varied after the image acquisition in order to decide on the optimal scatter rejection. This is not possible with the conventional radionuclide imaging technology employing a gamma camera or a rectilinear scanner. A gamma camera or rectilinear scanner is generally incapable of detecting and processing high intensity x-rays which are employed for high quality x-ray radiography.

If an image intensifier is not used, the scintillator can be in direct contact with the CCD. Alternatively, a fiberoptic reducer can be used between the CCD and the scintillator. Typical reduction ratios vary from 1:1 to 6:1 although the present embodiment is not limited to these ratios. Therefore, for a 20 mm×20 mm CCD, and a 6:1 fiberoptic reducer, the area of coverage will be about 120 mm. With a gated image intensifier or a shutter, the CCD does not receive any signal during the readout process. In a direct contact configuration, the use of frame transfer CCD as shown in FIG. 10 is preferred.

In applications utilizing x-ray transmission measurements a single frame is acquired for the recording of the x-rays emerging from the irradiated body of tissue. The CCD is operating in the integrating mode and each pixel or superpixel which accumulates a charge which is proportional to the total number of x-rays in this region without any energy discrimination. The resulting radiographic image can be combined electronically with the radionuclide image to form an accurate representation of both physiologic and anatomic information.

In the case of thin specimens examined in vitro a light source with wavelength ranging from the ultraviolet to near infrared can be used for the transmission image in the integrating mode. In this approach, the light shield in front of the scintillator is removed and the detector is placed in an enclosure to shield it from ambient light.

The present invention can thus combine radionuclide emission imaging and x-ray transmission imaging (radiography) using the same area detector with spectroscopic capability in the gamma-ray imaging mode. This camera can be operated utilizing both, the counting pulse-height analysis for gamma-ray imaging, and in the integrating or counting modes for x-ray transmission imaging. This enables exact superposition of the two images for accurate anatomic and physiologic imaging. Also, the operator can change the energy threshold even after the radionuclide image has been acquired. Thus, higher intrinsic spatial and energy resolution are provided than found in the conventional approachs.

While the invention has been particularly shown and described with reference to a preferred embodiment thereof, it will be understood by those skilled in the art that various changes in form and details can be made therein without departing from the spirit and scope of the invention as defined by the appended claims. The optical arrangements of FIG. 6 and FIG. 7 are just two examples of the various different optical arrangements that can be used. In addition, the orientation of the patient and the type of x-ray source used can be changed without departing from the spirit of the invention. Other types of screens and optical-enhancing means can be used, as can various CCD-controlling electronics and image processing systems.

I claim:

1. A method of x-ray imaging of a patient's body comprising:

providing an x-ray radiation source such that radiation emitted by the source is transmitted through the body to be imaged;

providing a charged coupled device (CCD) sensor to receive radiation from a scintillator that generates a spatial light intensity pattern in response to radiation emitted by the source and transmitted through the body;

providing an image intensifier between the radiation source and the CCD;

generating a discrete electronic representation of the spatial light intensity pattern from the radiation received by the CCD from the scintillator;

forming an image of the body from the analyzed representation.

2. The method of claim 1 wherein the radiation source comprises a dual energy source.

3. The method of claim 1 wherein the charged coupled device comprises a binnable CCD.

4. The method of claim 1 further comprising a data processor electrically connected to the CCD, the data processor having a memory in which the electronic representation is stored and a processing circuit that filters the electronic representation thereby providing a filtered image of bodily tissue.

5. The method of claim 1 further comprising performing pulse height analysis with the discrete electronic representation.

6. The method of claim 5 wherein the step of performing pulse height analysis comprises applying a filter to the discrete electronic representation, the filter having one or more selectable parameters.

7. The method of claim 6 wherein a selectable parameter comprises an energy range.

8. The method of claim 1 further comprising a fiber optic coupler between the scintillator and the CCD.

9. The method of claim 1 wherein the step of providing a CCD further comprises providing a frame transfer CCD.

10. The method of claim 1 further comprising scanning the body with a linear detector system.

11. The method of claim 1 further comprising providing a lens between the scintillator and the CCD.

12. The method of claim 1 further comprising providing a k-edge filter between the source and the CCD.

13. The method of claim 1 further comprising providing a CCD having a sensing area of 1 cm$^2$ or larger.

14. The method of claim 1 further comprising performing a rectilinear scan of the patient.

15. The method of claim 1 further comprising providing a C-arm to align the x-ray source and the detector.

16. The method of claim 1 further comprising detecting radiation from the source without cooling the CCD.

17. The method of claim 1 further comprising providing a shutter between the source and the CCD and controlling detection time with the shutter.

18. The method of claim 1 further comprising providing a mirror positioned between the radiation source and the CCD to reflect light along an optical path between the source and the CCD.

19. An x-ray bone densitometer for imaging bodily tissue comprising:

an x-ray radiation source that emits radiation that is transmitted through a portion of the bodily tissue;

a scintillator to receive radiation emitted by the source and transmitted through the portion of bodily tissue, the scintillator generating a spatial optical signal correlated with the received radiation;

a charge coupled device (CCD) that is optically coupled to the scintillator such that the CCD receives the spatial optical signal at a plurality of pixels and generates an electronic representation of the bodily tissue;

an antiscatter grid positioned between the radiation source and the charge coupled device;

a fiberoptic device to optically couple light emitted from the source to the charge coupled device; and a data processor electrically connected to the CCD, the processor having a memory in which the electronic representation is stored and a processing circuit that processes the electronic representation to provide an image of the bodily tissue.

20. The system for imaging bodily tissue of claim 19 wherein the radiation source further comprises a radionuclide that emits radiation having an energy in a range between 20 and 200 KeV.

21. The system for imaging bodily tissue of claim 19 wherein the radiation source emits radiation having an energy in the range between 10 and 2,000 KeV.

22. The system for imaging bodily tissue of claim 19 further comprising a controller electrically connected to the CCD.

23. A system for imaging bodily tissue comprising:

a radiation source that emits radiation that is transmitted through a portion of the bodily tissue;

a scintillator to receive radiation emitted by the source and transmitted through the portion of bodily tissue, the scintillator generating a spatial optical signal correlated with the received radiation;

a charge coupled device (CCD) that is optically coupled to the scintillator such that the CCD receives the spatial optical signal at a plurality of pixels and generates an electronic representation of the bodily tissue, the CCD being connected to the radiation source with a C-arm; and a data processor electrically connected to the CCD, the processor having a memory in which the electronic representation is stored and a processing circuit that filters the electronic representation to provide a filtered image of the bodily tissue, the processing circuit having a structure such that pixels with a measured intensity below a reference intensity are removed from the image.

24. The system for imaging bodily tissue of claim 23 wherein the radiation source further comprises a radionuclide that emits radiation having an energy in a range between 20 and 200 KeV.

25. The system for imaging bodily tissue of claim 23 further comprising an x-ray radiation source.

26. The system for imaging bodily tissue of claim 23 wherein the radiation source emits radiation having an energy in the range between 10 and 2,000 KeV.

27. The system for imaging bodily tissue of claim 23 further comprising a controller electrically connected to the CCD.

28. The system for imaging bodily tissue of claim 27 wherein the controller further comprises a gate control circuit such that the CCD receives radiation over a period of selectable duration, each period defining a frame that is delivered to the memory.

29. The system for imaging of bodily tissue of claim 28 further comprising an image intensifier positioned between the scintillator and the CCD, the intensifier being gated by the gate control circuit.

30. A method of performing a radiological examination of a subject, the method comprising:

providing a first radiation source to deliver a beam of x-rays toward the subject;

providing a second radiation source within the subject;

providing a scintillation screen to receive the radiation passing through the subject's body from the first radiation source, and to receive radiation emitted by the second radiation source, the screen emitting radiation with a first spatial intensity pattern proportional to the spatial intensity pattern of the x-ray radiation received from the first source and emitting a second spatial intensity pattern proportional to the spatial intensity pattern received from the second source;

detecting radiation emitted by the scintillation screen with a charge coupled device (CCD) sensor which generates a corresponding discretized electronic representation of the first and second spatial intensity patterns of the radiation emitted by the scintillation screen; and processing the discretized electronic representations generated by the CCD sensor with a CCD controller which provides corresponding first and second electronic images output.

31. The method of claim 30 wherein providing the first radiation source comprises providing an x-ray source which generates x-rays that are transmitted through the subject.

32. The method of claim 31 further comprising providing two energy levels from the x-ray source and filtering out one of the energy levels from the x-ray source during a portion of the radiological examination.

33. The method of claim 30 further comprising providing a radiation shield surrounding a region between the scintillation screen and the CCD sensor to prevent ambient radiation from reaching the CCD sensor.

34. The method of claim 30 further comprising focusing the radiation emitted from the scintillation screen with a focusing element which focuses said radiation onto the CCD sensor.

35. The method of claim 34 wherein focusing the radiation with a focusing element comprises focusing the radiation with a fiber optic reducer.

36. The method of claim 34 wherein focusing the radiation with a focusing element comprises focusing the radiation with a lens.

37. The method of claim 30 further comprising cooling the CCD sensor during operation of the CCD sensor.

38. The method of claim 30 further comprising storing the electronic image output of the CCD controller in an electronic image storage element.

39. The method of claim 30 further comprising binning together pixels of the CCD sensor to change the characteristics of the generated electronic representation.

40. The method of claim 30 further comprising filtering the second discretized electronic representation to discriminate between detected radiation that is above or below a threshold energy level.

41. A method of forming a radiographic image of body tissue or bone comprising:

providing a radiation source such that radiation emitted by the source is transmitted through the body to be imaged;

providing a charged coupled device (CCD) sensor to receive radiation emitted by the source and transmitted through the body;

generating a discrete electronic representation of a spatial intensity pattern from the radiation received by the CCD;

performing pulse height analysis on the discrete electronic representation to remove components of the representation having an intensity level below a selected reference intensity; and forming an image of the body from the analyzed representation.

42. The method of claim 41 wherein the radiation source comprises a dual energy source.

43. The method of claim 41 wherein the radiation source is an x-ray source.

44. The method of claim 41 wherein the charged coupled device comprises a binnable CCD.

45. The method of claim 41 further comprising a data processor electrically connected to the CCD, the data processor having a memory in which the electronic representation is stored and a processing circuit that filters the electronic representation thereby providing a filtered image of bodily tissue.

46. The method of claim 41 wherein the source comprises a radionuclide positioned within the body to be imaged.

47. The method of claim 41 further comprising generating a radiographic image and a radionuclide image.

48. The method of claim 47 further comprising superimposing the radiographic image with the radionuclide image.

49. The method of claim 41 further comprising selecting a second reference intensity and performing further pulse height analysis.

50. The method of claim 41 further comprising a fiber optic reducer between the scintillator and the CCD.

51. The method of claim 41 wherein the step of performing pulse height analysis comprises applying a filter to the discrete electronic representation, the filter having one or more selectable parameters.

52. The method of claim 51 wherein a selectable parameter comprises an energy range.

53. A method of performing x-ray densitometry comprising:

providing an x-ray radiation source such that radiation emitted by the source is transmitted through a portion of a patient's body to be imaged;

providing a charged coupled device (CCD) sensor to detect radiation from a scintillator in response to radiation from the source at two energies;

generating a discrete electronic representation of a spatial intensity pattern from the radiation received by the CCD;

forming an image of the body from the analyzed representation; and determining a density of bone within the body of the patient from the detected radiation.

54. The method of claim 53 further comprising providing a fiber optic reducer between the scintillator and the CCD.

55. The method of claim 54 wherein the step of performing pulse height analysis comprises applying a filter to the discrete electronic representation, the filter having one or more selectable parameters.

56. The method of claim 55 wherein a selectable parameter comprises an energy range.

57. The method of claim 53 further comprising selecting a second reference intensity and performing pulse height analysis.

58. The method of claim 53 wherein the radiation source comprises a dual energy source.

59. The method of claim 53 wherein the charged coupled device comprises a binnable CCD.

60. The method of claim 53 further comprising a data processor electrically connected to the CCD, the data processor having a memory in which the electronic representation is stored and a processing circuit that filters the electronic representation thereby providing a filtered image of bodily tissue.

* * * * *